United States Patent
Kelly et al.

(10) Patent No.: US 10,973,777 B2
(45) Date of Patent: Apr. 13, 2021

(54) METHODS FOR TREATMENT OF INTERSTITIAL CYSTITIS

(71) Applicant: Panag Pharma Inc., Halifax (CA)

(72) Inventors: Melanie Kelly, Ferguson's Cove (CA); Christian Lehmann, Halifax (CA); Mary Lynch, Halifax (CA)

(73) Assignee: Panag Pharma Inc., Halifax (CA)

( * ) Notice: Subject to any disclaimer, the term of this patent is extended or adjusted under 35 U.S.C. 154(b) by 0 days.

(21) Appl. No.: 16/190,450

(22) Filed: Nov. 14, 2018

(65) Prior Publication Data

US 2019/0142764 A1 May 16, 2019

Related U.S. Application Data

(60) Provisional application No. 62/586,516, filed on Nov. 15, 2017.

(51) Int. Cl.
| | | |
|---|---|---|
| *A61K 31/015* | (2006.01) | |
| *A61K 31/10* | (2006.01) | |
| *A61P 13/10* | (2006.01) | |
| *A61K 9/00* | (2006.01) | |
| *A61K 9/08* | (2006.01) | |

(52) U.S. Cl.
CPC .......... *A61K 31/015* (2013.01); *A61K 9/0014* (2013.01); *A61K 9/0053* (2013.01); *A61K 9/08* (2013.01); *A61K 31/10* (2013.01); *A61P 13/10* (2018.01)

(58) Field of Classification Search
CPC ........ A61K 31/015; A61K 31/10; A61P 13/10
See application file for complete search history.

(56) References Cited

FOREIGN PATENT DOCUMENTS

| WO | 2009140078 A1 | 11/2009 |
|---|---|---|
| WO | 2017039643 A1 | 3/2017 |

OTHER PUBLICATIONS

Marshall, K. Interstitial Cystitis: Understanding the Syndrome. Alternative Medicine Review. 8(4):426-437, 2003.
Z. Wang et al., "Treatment with a Cannabinoid Receptor 2 Agonist Decreases Severity of Established Cystitis" Journal of Urology 2014, 191:4, 1153-1158.
Z. Y. Wang et al., "Attenuation of Cystitis and Pain Sensation in Mice Lacking Fatty Acid Amide Hydrolase" J. Mol. Neurosci. 2015, 55:4, 968-976.
M. Yasuda et al., "Expression and function of fibronectin binding integrins on rat mast cells" International Immunology 1995, 7:2, 251-258.
Y. Yeh et al., "Effects of eritoran tetrasodium, a toll-like receptor 4 antagonist, on intestinal microcirculation in endotoxemic rats" Shock 2012, 37:5, 556-561.
N. Yoshimura et al., "Bladder afferent hyperexcitability in bladder pain syndrome/interstitial cystitis" International of Journal Urology 2014, 21:1, 18-25.
J.P. Zajicek et al., "Role of cannabinoids in multiple sclerosis" CNS Drugs 2011, 25:3, 187-201.
J. Zajicek, et al., "Cannabinoids for treatment of spasticity and other symptoms related to multiple sclerosis (CAMSstudy): multicentre randomised placebo-controlled trial" Lancet, 2003, 362, 1517-1526.
J. Zajicek, et al., "Cannabinoids in multiple sclerosis (CAMS) study: safety and efficacy data for 12 months follow up" J Neurol Neurosurg Psychiatry, 2005, 76, 1664-1669.
S. Akira et al., "Toll-Like Receptor Signalling" Nature Reviews Immunology 2004, 4, 499-511.
A. Aich et al., "Mast Cell-Mediated Mechanisms of Nociception" Int. J. Mol. Sci. 2015, 16, 29069-9092.
K.E. Andersson, "Potential Future Pharmacological Treatment of Bladder Dysfunction" Basic Clin. Pharmacol. Toxicol. 2016, 119, Suppl 3, 75-85.
M. Astiz et al., "Microvascular function and rheologic changes in hyperdynamic sepsis" Critical Care Medicine 1995, 23:2, 265-271.
S.B. Barker et al., "Prospective study of intravesical dimethyl sulphoxide in the treatment of chronic inflammatory bladder disease" British Journal of Urology, 1987, 59:2, 142-144.
S. Barr, "Diagnosis and management of interstitial cystitis" Obstet. Gynecol. Clin. North Am. 2014, 41:3, 397-407.
S. Belknap et al., "The Challenges of Interstitial Cystitis: Current Status and Future Prospects" Drugs 2015, 75:18, 2057-2063.
L. Birder et al., "Urothelial Signaling" Physiol. Rev. 2013, 93:2, 653-680.
D.E. Bjorling, et al., "Models of Inflammation of the Lower Urinary Tract" Neurourology and Urodynamics 2011, 30:5, 673-682.
Butawan et al., "Methylsulfonylmethane: Applications and safety of a novel dietary supplement" Nutrients 2017, 9, 290.
G.A. Cabral et al., "Emerging Role of the CB2 Cannabinoid Receptor in Immune Regulation and Therapeutic Prospects" Expert Reviews in Molecular Medicine 2009, 11, e3.
S.J. Childs, "Dimethyl sulfone (DMSO2) in the treatment of interstitial cystitis" Urol. Clin. N. Am. 1994, 21:1, 85-88.
I.M. Chiu et al., "Neurogenic inflammation and the peripheral nervous system in host defense and immunopathology". Nature Neuroscience 2012, 15:8, 1063-1067.
B.H. Choi et al., "Mast cell activation and response to tolterodine in the rat urinary bladder in a chronic model of intravesical protamine sulfate and bacterial endotoxin-induced cystitis" Mol. Med. Rep. 2014,10, 670-676.
S. Chuchawankul et al., "Role of cannabinoid receptors in inhibiting macrophage costimulatory activity" International Immunopharmacology 2004, 4:2, 265-278.
N. Clayton et al., "CB1 and CB2 cannabinoid receptors are implicated in inflammatory pain" Pain 2002, 96:3, 253-260.
J.Q. Clemens et al., "Prevalence and incidence of interstitial cystitis in a managed care population" J. Urol. 2005,173:1, 98-102.

(Continued)

*Primary Examiner* — James D. Anderson
(74) *Attorney, Agent, or Firm* — BERESKIN & PARR LLP/S.E.N.C.R.L., s.r.l.; Noel Courage

(57) ABSTRACT

The present application relates to methods and uses of CB2 target agent local anesthetics such as beta-caryophyllene for treatment of interstitial cystitis in a subject, optionally together with the administration or use of an additional agent for treating interstitial cystitis such as dimethyl sulfoxide (DMSO) or methylsulfonylmethane (MSM).

17 Claims, 14 Drawing Sheets

(56) References Cited

OTHER PUBLICATIONS

M. Colaco et al., "Current guidelines in the management of interstitial cystitis" Transl. Androl. Urol. 2015, 4:6, 677-83.
M. Costigan et al., "Neuropathic pain: a maladaptive response of the nervous system to damage" Annual Review of Neuroscience, 2009, 32, 1-32.
A. Cox et al., "CUA guideline: Diagnosis and treatment of interstitial cystitis/bladder pain syndrome" Can. Urol. Assoc. J. 2016, 10:5-6, E136-E155.
D.M. Daly et al., "The afferent system and its role in lower urinary tract dysfunction" Curr. Opin. Urol. 2011, 21:4, 268-74.
N.F. Davis et al., "Interstitial cystitis/painful bladder syndrome: epidemiology, pathophysiology and evidence-based treatment options" Eur. J. Obstet. Gynecol. Reprod. Biol. 2014, 175, 30-37.
P. Dinis, P. et al., "Anandamide-Evoked Activation of Vanilloid Receptor 1 Contributes to the Development of Bladder Hyperreflexia and Nociceptive Transmission to Spinal Dorsal Horn Neurons in Cystitis" J. Neurosci. 2004, 24, 11253-11263.
N. Dmitrieva et al., "Contrasting effects of WIN 55212-2 on motility of the rat bladder and uterus" J. Neurosci. 2002, 22:16, 7147-7153.
D.R. Erickson, "Interstitial Cystitis: Update on Etiologies and Therapeutic Options" Journal of Women's Health & Gender-Based Medicine 1999, 8:6, 745-758.
L. Facci et al., "Mast cells express a peripheral cannabinoid receptor with differential sensitivity to anandamide and palmitoylethanolamide" Proc. Natl. Acad. Sci. U. S. A. 1995, 92:8, 3376-80.
F. Facchinetti et al., "Cannabinoids Ablate Release of TNFalpha in Rat Microglial Cells Stimulated with Lypopolysaccharide" Glia 2003, 41:2, 161-168.
M. Fall et al., "Interstitial cystitis is bladder pain syndrome with Hunner's lesion" International Journal of Urology 2014, 21, 79-82.
W.P. Farquhar-Smith et al., "Attenuation of nerve growth factor-induced visceral hyperalgesia via cannabinoid CB1 and CB2-like receptors" Pain 2002, 97:1-2, 11-21.
O. Flores-Carreras et al., "Interstitial cystitis/painful bladder syndrome: diagnostic evaluation and therapeutic response in a private urogynecology unit" Transl. Androl. Urol. 2015, 4:6, 620-3.
J.E. Fowler, "Prospective study of intravesical dimethyl sulfoxide in treatment of suspected early interstitial cystitis" Urology 1981, 18:1, 21-26.
P.M. Galdino et al., "The anxiolytic-like effect of an essential oil derived from Spiranthera odoratissima A. St. Hil. leaves and its major component, β-caryophyllene, in male mice" Progress in Neuro-Psychopharmacology and Biological Psychiatry 2012, 38:2, 276-284.
J. Gertsch, et al., "Beta-caryophyllene is a dietary cannabinoid" Proceedings of the National Academy of Sciences of the United States of America, 2008 105:26, 9099-104.
C. Ghelardini et al., "Local anaesthetic activity of β-caryophyllene" II Farmaco 2001, 56, 387-389.
E. Graham et al., "Dysfunction of bladder urothelium and bladder urothelial cells in interstitial cystitis" Current Urology Reports 2006, 7:6, 440-446.
C. Gratzke et al., "Distribution and Function of Cannabinoid Receptors 1 and 2 in the Rat, Monkey and Human Bladder" J. Urol. 2009, 181:4, 1939-1948.
M. Green et al., "Expression of Intracellular Adhesion Molecules in the Bladder of Patients with Interstitial Cystitis" Urology 2004, 63:4, 688-693.
S. Grover et al., "Role of inflammation in bladder function and interstitial cystitis" Ther. Adv. Urol. 2011, 3:1, 19-33.
P. Hanno et al., "Status of International Consensus on Interstitial Cystitis/Bladder Pain Syndrome/Painful Bladder Syndrome: 2008 Snapshot" Neurourol. Urodyn. 2009, 28:4, 274-86.
M.H. Hayn et al., "Functional and Immunohistochemical Characterization of CB1 and CB2 Receptors in Rat Bladder" Urology 2008, 72:5, 1174-1178.
H.P. Horny et al., "Neoplastic human tissue mast cells express the adhesion molecule CD44/HCAM" Virchows Arch. 1996, 429:2-3, 91-94.
K. Horváth, et al., "Toxicity of methylsulfonylmethane in rats" Food and Chemical Toxicology 2002, 40, 1459-1462.
M. Hung et al., "Risk factors that affect the treatment of interstitial cystitis using intravesical therapy with a dimethyl sulfoxide cocktail" 2012, 23:11, 1533-1539.
S.I. Jaggar et al., "The anti-hyperalgesic actions of the cannabinoid anandamide and the putative CB2 receptor agonist palmitoylethanolamide in visceral and somatic inflammatory pain" Pain 1998, 76:1-2, 189-199.
A. Jerauld, "New Approaches in Managing Interstitial Cystitis/Bladder Pain Syndrome" US Pharmacist. 2016, 41:9, 29-33.
Y. Jiang et al., "Urothelial Dysfunction and Increased Suburothelial Inflammation of Urinary Bladder Are Involved in Patients with Upper Urinary Tract Urolithiasis—Clinical and Immunohistochemistry Study" PLoS One 2014, 9:10, e110754.
J.L. Jordan et al., "Use of a Sulfated Chitosan Derivative to Reduce Bladder Inflammation in the Rat" Urology 2007, 70:5, 1014-1018.
S. Keay, "Cell signaling in interstitial cystitis/painful bladder syndrome" Cell. Signal. 2008, 20:12, 2174-2179.
H.J. Kim, "Update on the Pathology and Diagnosis of Interstitial Cystitis / Bladder Pain Syndrome: A Review" Int. Neurourol. J. 2016, 20:1, 13-17.
A.-L. Klauke et al., "The cannabinoid CB2 receptor-selective phytocannabinoid beta-caryophyllene exerts analgesic effects in mouse models of inflammatory and neuropathic pain" European Neuropsychopharmacology, 2014, 24:4, 608-620.
T.W. Klein, "Cannabinoid-based drugs as anti-inflammatory therapeutics. Nature Reviews Immunology" Nature Rev. Immunol. 2005, 5:5, 400-411.
H. Krenn et al., "A case of cannabinoid rotation in a young woman with chronic cystitis" J. Pain Symptom Manage. 2003, 25:1, 3-4.
R. Kumar et al., "Comparative antinociceptive effect of arachidonylcyclopropylamide, a cannabinoid 1 receptor agonist & lignocaine, a local anaesthetic agent, following direct intrawound administration in rats" Indian J Med Res Nov. 2016, 144, 730-740.
C.-L. Lee et al., "Long-Term Efficacy and Safety of Repeated Intravescial OnabotulinumtoxinA Injections Plus Hydrodistention in the Treatment of Interstitial Cystitis/Bladder Pain Syndrome" Toxins (Basel), 2015, 7:10, 4283-4293.
C. Lehmann et al., "Cannabinoid receptor 2 activation reduces intestinal leukocyte recruitment and systemic inflammatory mediator release in acute experimental sepsis" Critical Care 2012, 16:2, R47.
F.C. Leong, "Complementary and alternative medications for chronic pelvic pain" Obs. Gynecol Clin N Am 2014, 41:3, 503-510.
Y.N. Lim, et al., "Long-term outcomes of intravesical dimethyl sulfoxide/heparin/hydrocortisone therapy for interstitial cystitis/bladder pain syndrome" International Urogynecology Journal 2017, 28:7, 1085-1089.
H. Liu et al., "Biomarkers for patients with interstitial cystitis/bladder pain syndrome" Urological Science 2015, 26:4, 225-229.
A. Luchicchi et al., "Anandamide and 2-arachidonoylglycerol: Pharmacological properties, functional features, and emerging specificities of the two major endocannabinoids" Molecular Neurobiology 2012, 46:2, 374-392.
G. Marone et al., "Probing the roles of mast cells and basophils in natural and acquired immunity, physiology and disease" Trends in Immunology 2002, 23:9, 425-427.
E. Martin et al., "Underlying Mechanisms and Optimal Treatment for Interstitial Cystitis: A Brief Overview" Urologic Nursing 2015, 35:3, 111-116.
R.S. Martin et al., "Effects of cannabinoid receptor agonists on neuronally-evoked contractions of urinary bladder tissues isolated from rat, mouse, pig, dog, monkey and human" Br. J. Pharmacol. 2000, 129:8, 1707-15.
R. Mayer, "Interstitial cystitis pathogenesis and treatment" Curr. Opin. Infect. Dis. 2007, 20:1, 77-82.
M.T. McLennan, "Interstitial cystitis: Epidemiology, pathophysiology, and clinical presentation" Obstet. Gynecol. Clin. North Am. 2014, 41:3, 385-395.

(56) References Cited

OTHER PUBLICATIONS

J. McCurdy et al., "Toll-like receptor 4-mediated activation of murine mast cells" Journal of Leukocyte Biology 2001, 70:6, 977-984.
F. Merriam et al., "Cannabinoid receptor 2 is increased in acutely and chronically inflamed bladder of rats" Neuroscience Letters 2008, 445:1, 130-134.
F.V. Merriam et al., "Inhibition of fatty acid amide hydrolase suppresses referred hyperalgesia induced by bladder inflammation" BJU Int. 2011, 108:7, 1145-1149.
L. Merrill et al., "Receptors, channels, and signalling in the urothelial sensory system in the bladder" Nat. Rev. Urol. 2016, 13:4, 193-204.
F. Molina-Holgado et al., "Role of CB 1 and CB 2 Receptors in the Inhibitory Effects of Cannabinoids on Lipopolysaccharide-Induced Nitric Oxide Release in Astrocyte Cultures" J. Neurosci. Res. 2002, 67:6, 829-836.
D. Fernández-López et al., "The Cannabinoid Agonist Win55212 Reduces Brain Damage in an in Vivo Model of Hypoxic-Ischemic Encephalopathy in Newborn Rats" Pediatric Research, 2007, 62:3, 255-260.
G. Mukerji et al., "Increased Cannabinoid Receptor 1-Immunoreactive Nerve Fibers in Overactive and Painful Bladder Disorders and Their Correlation With Symptoms" Urology 2010, 75:6, 1514.e15-20.
S. Munro et al., Molecular Characterization of a peripheral receptor for cannabinoids. Nature 1993, 365:6441, 61-65.
O. Nilsson et al., "The cannabinoid agonist WIN 55,212-2 inhibits TNF-alpha-induced neutrophil transmigration across ECV304 cells" European Journal of Pharmacology 2006, 547:1-3, 165-173.
P. Pacher et al., "The Endocannabinoid System as an Emerging Target of Pharmacotherapy" Pharmacological Reviews 2006, 58:3, 389-462.
R. Pandey et al., "Endocannabinoids and immune regulation" Pharmacol Res 2009, 60:2, 85-92.
C. Parsons et al., "A quantitatively controlled method to study prospectively interstitial cystitis and demonstrate the efficacy of pentosanpolysulfate" Journal of Urology 1993, 150:3, 845-848.
R. Perez-Marrero et al., "A controlled study of dimethyl sulfoxide in interstitial cystitis" The Journal of Urology 1988, 140:1, 36-39.
R.G. Pertwee, "Cannabinoid pharmacology: the first 66 years" Br J Pharmacol 2006, 147 Suppl 1, S163-71.
R.G. Pertwee, "The pharmacology of cannabinoid receptors and their ligands: an overview" International Journal of Obesity 2006, 30, Suppl. 1, S13-18.
R.G. Pertwee et al., "Evidence for the presence of cannabinoid CB1 receptors in mouse urinary bladder" Br. J. Pharmacol. 1996, 118:8, 2053-8.
R.G. Pertwee et al., "Cannabinoid receptors and their ligands" Prostaglandins Leukot Essent Fatty Acids 2002, 66:2-3, 101-121.
F. Pessina et al., "Protective effect of palmitoylethanolamide in a rat model of cystitis" J. Urol. 2015, 193:4, 1401-1408.

W.F. Rawls et al., "Dimethyl sulfoxide (DMSO) as intravesical therapy for interstitial cystitis/bladder pain syndrome: A review" Neurourol. Urodyn. 2017, 36:7, 1677-1684.
P.H. Reggio, "Endocannabinoid structure-activity relationships for interaction at the cannabinoid receptors" Prostaglandins, Leukot. Essent. Fatty Acids 2002, 66:2-3, 143-160.
T.R.L. Romero et al., "CB1 and CB2 Cannabinoid Receptor Agonists Induce Peripheral Antinociception by Activation of the Endogenous Noradrenergic System" Anethesia & Analgesia, 2013, 116:2, 463-472.
J. Rössberger et al., "Critical appraisal of dimethyl sulfoxide treatment for interstitial cystitis discomfort, side-effects and treatment outcome" Scandinavian J. Urol. Nephrol. 2005, 39:1, 73-77.
G.R. Sant et al., "The Mast Cell in Interstitial Cystitis: Role in Pathophysiology and Pathogenesis" Urology 2007, 69:4 Suppl., 34-40.
J. Sardinha et al., "Experimental Cannabinoid 2 Receptor-Mediated Immune Modulation in Sepsis" Mediators of Inflammation 2014, Article ID 978678.
S.W. Shirley et al., "Dimethyl sulfoxide in treatment of inflammatory genitourinary disorders" Urology 1978, 11:3, 215-220.
P.E. Spronk et al., "Bench-to-bedside review: sepsis is a disease of the microcirculation" Critical Care 2004, 8:6, 462-468.
H. Suzuki et al., "Substance P induces degranulation of mast cells and leukocyte adhesion to venular endothelium" Peptides 1995, 16:8, 1447-1452.
S. Tambaro et al., "Evaluation of selective cannabinoid CB(1) and CB(2) receptor agonists in a mouse model of lipopolysaccharide-induced interstitial cystitis" European Journal of Pharmacology 2014, 729, 67-74.
C. Theoharides et al., "Mast cell involvement in interstitial cystitis: a review of human and experimental evidence" Urology 2001, 57:6, 47-55.
J.T. Toguri et al., "Cannabinoid 2 receptor activation reduces leukocyte adhesion and improves capillary perfusion in the iridial microvasculature during systemic inflammation" Clin. Hemorheol. Microcirc. 2015, 61:2, 237-249.
V. Tyagi et al., "Differential Expression of Functional Cannabinoid Receptors in Human Bladder Detrusor and Urothelium" J. Urol. 2009, 181:4, 1932-1938.
J.-S. Walczak et al., "Local activation of cannabinoid CB1 receptors in the urinary bladder reduces the inflammation-induced sensitization of bladder afferents" Mol. Pain 2011, 7:31.
J.S. Walczak et al., "Cannabinoid CB1 receptors are expressed in the mouse urinary bladder and their activation modulates afferent bladder activity" Neuroscience 2009, 159, 1154-1163.
X. Wang et al., "Evidence for the Role of Mast Cells in Cystitis-Associated Lower Urinary Tract Dysfunction: A Multidisciplinary Approach to the Study of Chronic Pelvic Pain Research Network Animal Model Study" PLoS One 2016, 11:12, e0168772.
Z.-Y. Wang et al., "Activation of Cannabinoid Receptor 1 Inhibits Increased Bladder Activity Induced by Nerve Growth Factor" Neuroscience Letters 2015, 589, 19-24.
Z-Y. Wang, et al., "Activation of cannabinoid receptor 2 inhibits experimental cystitis" American Journal of Physiology. Regulatory, Integrative and Comparative Physiology, 2013, 304, R846-R853.

METHODS FOR TREATMENT OF INTERSTITIAL CYSTITIS

CROSS-REFERENCE TO RELATED APPLICATIONS

The present application claims the benefit of priority from U.S. provisional application No. 62/586,516 filed on Nov. 15, 2017, the contents of which are incorporated herein by reference in their entirety.

FIELD

The present application relates to the use of CB2 target agent local anesthetics such as beta-caryophyllene for treatment of interstitial cystitis.

BACKGROUND

Interstitial cystitis (IC) is a chronic inflammatory disorder of the urinary bladder in the absence of an infection. The symptoms of IC include pelvic pain, a persistent urge to void and urinary frequency. The prevalence and incidence of IC tends to be higher in women than men, for example, the female-to-male ratio has been reported to be 5:1.[1] IC is recognized as a disease which may cause profound negative effects on patients' quality of life. However, to date, despite decades of basic science research, no definite pathophysiology has been identified and standard treatment options are still lacking.

Current treatments for interstitial cystitis are most commonly oral medications or bladder instillations. The most commonly used oral therapies, such as pentosan polysulfate (PPS) and tricyclic antidepressants, have been found to be beneficial in relieving some symptoms in a proportion of patients with IC, but not all patients gain therapeutic benefit from these approaches[2]. For example, one study revealed that the effect of PPS treatment was limited to only a quarter of patients.[3] Another study that trialed PPS and tricyclic anti-depressant treatments along with other adjuvant treatments for more than a year, found the symptoms of IC remained unchanged or had relapsed.[4]

Intravesical therapies have provided some relief to patients where the pharmacological agent is delivered directly into the bladder. Dimethyl sulfoxide (DMSO) is one such pharmacological agent commonly used for IC instillations[5] and is FDA approved. DMSO has been reported to have anti-inflammatory effects, and ability to stabilize mast cells.[2] Unfortunately, despite some initial relief, symptom relapse in IC is common. For example, DMSO treatment has a high failure rate in patients with severe IC.[6] Methylsulfonylmethane (MSM; other names include dimethyl sulfone, methyl sulfone, sulfonylbismethane, organic sulfur, crystalline dimethyl sulfoxide and $DMSO_2$) has also been reported in clinical case studies for IC and was reported to be an effective treatment for 4 out of 6 patients suffering from IC.[7] Methylsulfonylmethane has been designated GRAS by the FDA The endogenous cannabinoid system (ECS) is involved in a variety of physiological processes including but not limited to metabolism, pain-sensation, neurotransmission and inflammation.[8] The ECS is made up of cannabinoid receptors (both endogenous cannabinoid 1 (CB1) and cannabinoid 2 (CB2) receptors), endogenous cannabinoids (EC; such as N-arachidonoylethanolamine or anandamide (AEA) and 2 arachidonoylglycerol (2-AG)), and endocannabinoid metabolizing enzymes[8](a). CB1 receptors are expressed in the central nervous system (CNS) and non-neural peripheral tissues.[9] CB2 receptors are highly localized to immune cells with limited distribution reported for selected CNS areas and some peripheral tissues, such as intestine and bladder.[10] In addition to activation by endogenous ligands, cannabinoid receptors are the target for phytocannabinoids and derivatives. To-date, several synthetic ligands have been developed that selectively bind to CB1 or CB2 receptors.[11]

The role of the ECS in modulating the immune response has been actively studied by researchers for more than twenty years.[12] However, only a few studies have focused on the functional role of cannabinoid receptors in relation to the urinary bladder. For example, therapeutic effects of cannabinoids (oral synthetic $\Delta^9$-tetrahydrocannabinol ($\Delta^9$-THC) or *cannabis* extract containing $\Delta^9$-THC and cannabidiol (CBD) as the main cannabinoids) on bladder control in multiple sclerosis patients were reported with findings from the CAMS study.[13] There is also evidence of the presence of the cannabinoid receptors CB1 and CB2 in bladders of various species, including rodents, monkeys and humans.[14] Another study investigated the effect of the synthetic cannabinoid receptor ligand GP1a (a selective CB2 agonist) as a therapeutic agent in the treatment of cystitis-induced inflammation of bladder.[15] Systemic administration of the endocannabinoid, AEA, or the fatty acid ethanolamine, N-palmitoyletanolamide (PEA), attenuated local nerve growth factor (NGF)-induced bladder hyper-reflexia and reduction of micturition threshold in rats.[16] The effect of AEA was blocked by antagonism of CB1 and CB2 receptors, indicating that the action of the endocannabinoid, AEA, was mediated by both CB1 and CB2, whereas the effect of PEA was largely due to CB2. An older study also reported on the cannabinoid receptor-mediated effect of PEA in turpentine induced bladder hyper-reflexia.[17] Tambaro et al. have investigated the use of an orthosteric cannabinoid ligand (JWH015) in a model of LPS-induced IC.[18] There have been a few other studies examining the involvement of CB2 receptors in immune responses in experimental cystitis[19].

Beta-caryophyllene (Beta-C) is a natural dietary sesquiterpenoid that acts as an agonist at CB2 receptors and is found in abundant concentrations in many food plants, such as oregano and cinnamon, as well as in *cannabis*. Beta-C has been shown to exert analgesic and anti-inflammatory effects in mouse models of inflammatory and neuropathic pain[20], and additionally also exhibits dose-dependent local anesthetic actions comparable to procaine[21].

SUMMARY

In a systemic bladder inflammation model, administration of Beta-C significantly decreased the number of adhering leukocytes and restored perfusion in functional capillaries in the bladder microcirculation to levels observed in healthy control animals following endotoxin challenge. In a local bladder inflammation model, administration of Beta-C by instillation decreased leukocyte adhesion, restored leukocyte rolling and restored functional capillary density. Administration of Beta-C orally also reduced leukocyte adherence in the local bladder inflammation model and increased functional capillary density in control animals. Oral Beta-C administration was also found to improve breathing rate, eye opening, motor activity and posture scores, reduced the behavioural pain score and increased the pain withdrawal threshold in the experimental cystitis model used in the present studies.

Accordingly, the present application includes a method of treating interstitial cystitis in a subject, the method comprising administering a CB2 target agent local anaesthetic to the subject. The present application also includes a use of a CB2 target agent local anaesthetic for treatment of interstitial cystitis in a subject. The present application also includes a use of a CB2 target agent local anaesthetic for preparation of a medicament for treatment of interstitial cystitis in a subject. The present application also includes a CB2 target agent local anaesthetic for use to treat interstitial cystitis in a subject. In an embodiment of the present application, the CB2 target agent local anaesthetic is beta-caryophyllene.

Accordingly, the present application also includes a method of treating interstitial cystitis in a subject, the method comprising administering beta-caryophyllene to the subject. The present application also includes a use of beta-caryophyllene for treatment of interstitial cystitis in a subject. The present application also includes a use of beta-caryophyllene for preparation of a medicament for treatment of interstitial cystitis in a subject. The present application also includes beta-caryophyllene for use to treat interstitial cystitis in a subject.

In a local bladder inflammation model, the combination of Beta-C with DMSO treatment significantly decreased the number of adhering leukocytes whereas DMSO treatment alone did not significantly decrease leukocyte adherence. Beta-C in 5% DMSO instillation yielded the lowest overall values for leukocyte adherence. Similarly, administration of Beta-C with DMSO restored perfusion in functional capillaries in the bladder microcirculation to levels observed in healthy control animals following endotoxin challenge whereas DMSO treatment did not. In a local bladder inflammation model, the combination of Beta-C with DMSO instillation improved the rolling flux number, when compared to the untreated group and restored capillary perfusion to levels observed in healthy control animals. Methylsulfonylmethane (MSM) has actions similar to DMSO but may be advantageous, for example, as it has reduced scent in comparison to DMSO. In a local bladder inflammation model, oral administration of Beta-C and MSM reduced leukocyte adherence and improved functional capillary density. Oral administration of Beta-C in combination with MSM instillation reduced leukocyte adherence, restored leukocyte rolling and restored functional capillary density in the local bladder inflammation model.

Accordingly, in some embodiments of the method for treating interstitial cystitis in the subject, the method further comprises administering an additional agent for treating interstitial cystitis to the subject. Similarly, in some embodiments of the uses of the present application, the CB2 target agent local anaesthetic (e.g. beta-caryophyllene) is for use in combination with an additional agent for treating interstitial cystitis; i.e. the use further comprises the use of an additional agent for treating interstitial cystitis in the subject. In some embodiments of the present application, the additional agent for treating interstitial cystitis is dimethyl sulfoxide (DMSO) or methylsulfonylmethane (MSM). In an embodiment, the additional agent for treating interstitial cystitis is dimethyl sulfoxide (DMSO). In another embodiment, the additional agent for treating interstitial cystitis is methylsulfonylmethane (MSM).

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

BRIEF DESCRIPTION OF THE DRAWINGS

The embodiments of the application will now be described in greater detail with reference to the attached drawings in which.

DETAILED DESCRIPTION

I. Definitions

Figure 1:
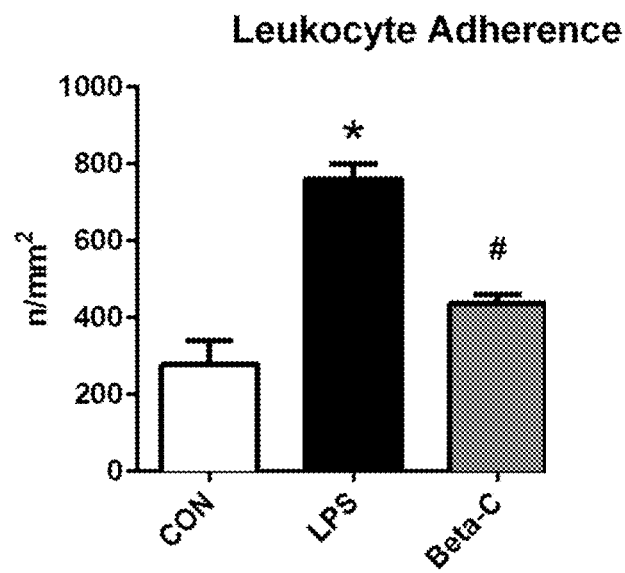
FIG. 1 is a plot showing leukocyte adhesion (n/mm$^2$) in bladder venules of female CD-1 mice for a lipopolysaccharide (LPS)-induced cystitis model treated with beta-caryophyllene (Beta-C) in comparison to healthy controls (CON) and untreated LPS-induced cystitis (LPS). Data presented as mean±SD.

Unless otherwise indicated, the definitions and embodiments described in this and other sections are intended to be applicable to all embodiments and aspects of the present application herein described for which they are suitable as would be understood by a person skilled in the art.

The present application refers to a number of chemical terms and abbreviations used by those skilled in the art. Nevertheless, definitions of selected terms are provided for clarity and consistency.

As used herein, the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process/method steps. As used herein, the word "consisting" and its derivatives, are intended to be close ended terms that specify the presence of stated features, elements, components, groups, integers, and/or steps, and also exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise.

The term "and/or" as used herein means that the listed items are present, or used, individually or in combination. In effect, this term means that "at least one of" or "one or more" of the listed items is used or present.

The term "CB2 target agent local anaesthetic" as used herein refers to a compound that binds, activates and/or increases the activation of the CB2 receptor and additionally has local anaesthetic actions.

The term "CB2 orthosteric agonist agent local anaesthetic" as used herein refers to a compound that acts as an orthosteric agonist at the CB2 receptor and additionally has local anaesthetic actions.

The terms "beta-caryophyllene", "Beta-C" or "BCP" and the like as used herein refer to a compound having the following chemical structure:

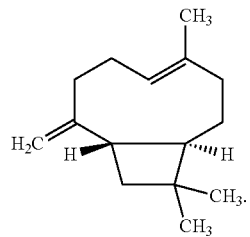

The term "pharmaceutically acceptable" means compatible with the treatment of subjects, for example, mammals such as humans.

The term "parenteral" as used herein means taken into the body or administered or used in a manner other than through the gastrointestinal tract.

The term "enteral" as used herein means taken into the body or administered or used in manner that is through the gastrointestinal tract.

The term "subject" as used herein includes all members of the animal kingdom including mammals. In an embodiment, the subject is a human. In another embodiment of the present application, the subject is female.

The terms "to treat", "treating" and "treatment" as used herein and as is well understood in the art, means an approach for obtaining beneficial or desired results, including clinical results. Beneficial or desired clinical results include, but are not limited to alleviation or amelioration of one or more symptoms of interstitial cystitis, diminishment of the extent of the interstitial cystitis, stabilized (i.e., not worsening) interstitial cystitis, delay or slowing of the progression of interstitial cystitis, amelioration or palliation of the disease state of the interstitial cystitis, diminishment of the reoccurrence of the interstitial cystitis, and/or remission (whether partial or total) of the interstitial cystitis, whether detectable or undetectable. "To treat", "treating" and "treatment" as used herein also include prophylactic treatment of the interstitial cystitis. For example, a subject with early stage interstitial cystitis is treated to prevent progression or alternatively a subject in remission is treated to prevent recurrence.

The term "administered" as used herein means administration of an effective amount of a CB2 target agent local anaesthetic (e.g. beta-caryophyllene) and optionally the additional agent for treating interstitial cystitis (e.g. DMSO or MSM) to a cell either in cell culture or in a subject.

As used herein, the term "effective amount" or "therapeutically effective amount" means an amount effective, at dosages and for periods of time necessary to achieve a desired result. For example, in the context of treating interstitial cystitis, an effective amount of the CB2 target agent local anaesthetic (e.g. beta-caryophyllene) and optionally the additional agent for treating interstitial cystitis (e.g. DMSO or MSM) is an amount that, for example, reduces the interstitial cystitis compared to the interstitial cystitis without administration of the CB2 target agent local anaesthetic and optionally the additional agent for treating interstitial cystitis. By "reducing the interstitial cystitis", it is meant, for example, reducing the symptoms or effects of the interstitial cystitis such as urothelial dysfunction, neurogenic inflammation and/or neuropathic pain. Effective amounts may vary according to factors such as the disease state, age, sex and/or weight of the subject. The amount of a CB2 target agent local anaesthetic (e.g. beta-caryophyllene) and optionally the additional agent for treating interstitial cystitis (e.g.

DMSO or MSM) that will correspond to such an amount will vary depending upon various factors, such as the given CB2 target agent local anaesthetic (or optionally the additional agent for treating interstitial cystitis, if administered or used), the pharmaceutical formulation, the route of administration or use, the identity of the subject being treated, and the like, but can nevertheless be routinely determined by one skilled in the art.

The term "urothelial dysfunction" as used herein refers to dysfunction of bladder urothelium and bladder urothelial cells.[22] Urothelial dysfunction may involve multiple abnormalities in bladder urothelial physiology and may, for example, be a feature in the pathophysiology of interstitial cystitis.

The term "neurogenic inflammation" as used herein refers to inflammation arising from the local release of inflammatory mediators from sensory nerve terminals of afferent neurons such as but not limited to Substance P, Calcitonin Gene-Related Peptide, neurokinin A, and endothelin-3 and may, for example, be a feature in the pathophysiology of interstitial cystitis.[23] TRPA1 channels stimulated by LPS may also cause neurogenic inflammation.

The term "neuropathic pain" as used herein refers to pain caused by damage and/or disease affecting the somatosensory nervous system and may, for example, be a feature in the pathophysiology of interstitial cystitis.[24]

II. Methods and Uses

In a systemic bladder inflammation model, administration of Beta-C significantly decreased the number of adhering leukocytes and restored perfusion in functional capillaries in the bladder microcirculation to levels observed in healthy control animals following endotoxin challenge. In a local bladder inflammation model, administration of Beta-C by instillation decreased leukocyte adhesion, restored leukocyte rolling and restored functional capillary density. Administration of Beta-C orally also reduced leukocyte adherence in the local bladder inflammation model and increased functional capillary density in control animals. Oral Beta-C administration was also found to improve breathing rate, eye opening, motor activity and posture scores, reduced the behavioural pain score and increased the pain withdrawal threshold in the experimental cystitis model used in the present studies.

Accordingly, the present application includes a method of treating interstitial cystitis in a subject, the method comprising administering a CB2 target agent local anaesthetic to the subject. The present application also includes a use of a CB2 target agent local anaesthetic for treatment of interstitial cystitis in a subject. The present application also includes a use of a CB2 target agent local anaesthetic for preparation of a medicament for treatment of interstitial cystitis in a subject. The present application also includes a CB2 target agent local anaesthetic for use to treat interstitial cystitis in a subject.

In an embodiment, the CB2 target agent local anaesthetic is a CB2 orthosteric agonist agent local anaesthetic. In another embodiment, the CB2 orthosteric agonist agent local anaesthetic is beta-caryophyllene. In another embodiment, the CB2 target agent local anaesthetic is beta-caryophyllene.

Accordingly, the present application also includes a method of treating interstitial cystitis in a subject, the method comprising administering beta-caryophyllene to the subject. The present application also includes a use of beta-caryophyllene for treatment of interstitial cystitis in a subject. The present application also includes a use of beta-caryophyllene for preparation of a medicament for treatment of interstitial cystitis in a subject. The present application also includes beta-caryophyllene for use to treat interstitial cystitis in a subject.

In a local bladder inflammation model, the combination of Beta-C with DMSO treatment significantly decreased the number of adhering leukocytes whereas DMSO treatment alone did not significantly decrease leukocyte adherence. Beta-C in 5% DMSO instillation yielded the lowest overall values for leukocyte adherence. Similarly, administration of Beta-C with DMSO restored perfusion in functional capillaries in the bladder microcirculation to levels observed in healthy control animals following endotoxin challenge whereas DMSO treatment did not. In a local bladder inflammation model, the combination of Beta-C with DMSO instillation improved the rolling flux number, when compared to the untreated group and restored capillary perfusion to levels observed in healthy control animals. Methylsulfonylmethane (MSM) has actions similar to DMSO but may be advantageous, for example, as it has reduced scent in comparison to DMSO. In a local bladder inflammation model, oral administration of Beta-C and MSM reduced leukocyte adherence and improved functional capillary density. Oral administration of Beta-C in combination with MSM instillation reduced leukocyte adherence, restored leukocyte rolling and restored functional capillary density in the local bladder inflammation model.

Accordingly, in some embodiments of the method for treating interstitial cystitis in the subject, the method further comprises administering an additional agent for treating interstitial cystitis to the subject. Similarly, in some embodiments of the uses of the present application, the CB2 target agent local anaesthetic (e.g. beta-caryophyllene) is for use in combination with an additional agent for treating interstitial cystitis; i.e. the use further comprises the use of an additional agent for treating interstitial cystitis in the subject. In some embodiments of the present application, the additional agent for treating interstitial cystitis is dimethyl sulfoxide (DMSO) or methylsulfonylmethane (MSM). In an embodiment, the additional agent for treating interstitial cystitis is dimethyl sulfoxide (DMSO). In another embodiment, the additional agent for treating interstitial cystitis is methylsulfonylmethane (MSM).

The CB2 target agent local anaesthetic (e.g. beta-caryophyllene) is administered to a subject or used in a variety of forms depending on the selected route of administration or use, as will be understood by those skilled in the art. In an embodiment, the CB2 target agent local anaesthetic is administered to the subject or used, for example, by enteral or parenteral routes, and the CB2 target agent local anaesthetic formulated accordingly. Conventional procedures and ingredients for the selection and preparation of suitable compositions are described, for example, in Remington's Pharmaceutical Sciences (2000-20th edition) and in The United States Pharmacopeia: The National Formulary (USP 24 NF19) published in 1999.

Enteral administration or use includes all routes involving the gastrointestinal tract, for example, oral, buccal, sublingual, nasal and rectal. In an embodiment of the present application, the enteral administration or use of the CB2 target agent local anaesthetic is oral administration or use; i.e. the CB2 target agent local anaesthetic is administered orally or is for oral use, as the case may be. Formulations suitable for oral administration or use may be prepared by methods known to a person skilled in the art. In some embodiments, the CB2 target agent local anaesthetic is orally administered or for oral use in the form of a capsule comprising the CB2 target agent local anaesthetic.

Parenteral administration or use includes intravesical, intravenous, intraperitoneal, subcutaneous, intramuscular, transepithelial, intrapulmonary, intrathecal, and topical modes of administration or use. Formulations suitable for parenteral administration or use are prepared by known methods by a person skilled in the art. In an embodiment, the parenteral administration or use of the CB2 target agent local anaesthetic is intravesical administration or use; i.e. the CB2 target agent local anaesthetic is administered intravesically or is for intravesical use, as the case may be. For example, in some embodiments wherein the CB2 target agent local anaesthetic is administered or for use in combination with dimethyl sulfoxide (DMSO) or methylsulfonylmethane (MSM), the intravesical administration is in the form of an aqueous solution comprising the CB2 target agent local anaesthetic and the dimethyl sulfoxide (DMSO) or methylsulfonylmethane (MSM). Alternatively, in some embodiments, the CB2 target agent local anaesthetic is administered or for use intravesically dissolved in another suitable solvent for intravesical use, the selection of which can be made by a person skilled in the art. In another embodiment, the parenteral administration or use of the CB2 target agent local anaesthetic is topical administration or use; i.e. the CB2 target agent local anaesthetic is administered topically or is for topical use, as the case may be. Formulations suitable for topical administration or use may be prepared by methods known to a person skilled in the art. In an embodiment, the CB2 target agent local anaesthetic is administered or for use in a topical cream; i.e. the topical administration or use is in the form of a topical cream comprising the CB2 target agent local anaesthetic. Such topical creams also contain suitable non-medicinal ingredients.

The additional agent for treating interstitial cystitis is formulated and administered or used via any suitable route or dosage form known in the art which may depend, for example, on the identity of the agent. In embodiments where the additional agent for treating interstitial cystitis is DMSO, the administration or use is intravesical administration or use. DMSO formulations suitable for intravesical administration or use may be prepared by methods known to a person skilled in the art. In an embodiment, the DMSO is administered or for use as an aqueous solution comprising about 40% or about 50% dimethyl sulfoxide. In another embodiment, the DMSO is administered or for use as an aqueous solution comprising from about 1% to about 60% or about 5% to about 50% dimethyl sulfoxide. In a further embodiment, the DMSO is administered or for use as an aqueous solution comprising from about 1% to about 10% or about 5% DMSO. In another embodiment, the DMSO is administered or for use as an aqueous solution comprising from about 35% to about 45% or about 40% DMSO. In a further embodiment, the DMSO is administered or for use as an aqueous solution comprising from about 45% to about 55% or about 50% DMSO. In some embodiments where the additional agent for treating interstitial cystitis is MSM, the administration or use is intravesical administration or use. MSM formulations suitable for intravesical administration or use may be prepared by methods known to a person skilled in the art. In an embodiment, the MSM is administered or for use as an aqueous solution comprising about 40% or about 50% methylsulfonylmethane. In another embodiment, the MSM is administered or for use as an aqueous solution comprising from about 1% to about 60% or about 5% to about 50% MSM. In a further embodiment, the MSM is administered or for use as an aqueous solution comprising from about 1% to about 10% or about 5% MSM. In another embodiment, the MSM is administered or for use as an aqueous solution comprising from about 35% to about 45% or about 40% MSM. In a further embodiment, the MSM is administered or for use as an aqueous solution comprising from about 45% to about 55% or about 50% MSM. It will be appreciated by a person skilled in the art that in such formulations for intravesical installation, the water is pharmaceutically acceptable water. In other embodiments where the additional agent for treating interstitial cystitis is MSM, the administration or use is oral administration or use; i.e. MSM is administered orally or is for oral use, as the case may be. Formulations suitable for oral administration or use may be prepared by methods known to a person skilled in the art. In some embodiments, the MSM is orally administered or for oral use in the form of a capsule comprising the MSM. In some embodiments of the present application, the capsule comprises the MSM and the CB2 target agent local anaesthetic (e.g. beta-C).

Treatment methods comprise administering to a subject or use of the CB2 target agent local anaesthetic (and optionally the additional agent for treating interstitial cystitis) and optionally consist of a single administration or use, or alternatively comprise a series of administrations or uses. The length of the treatment period depends on a variety of factors, such as the severity of the interstitial cystitis, the age and/or the sex of the subject, the activity and/or formulation of the CB2 target agent local anaesthetic, the identity and/or formulation of the additional agent for treating interstitial cystitis and/or a combination thereof.

In embodiments wherein the CB2 target agent local anaesthetic is administered or for use with the additional agent for treating interstitial cystitis, CB2 target agent local anaesthetic and the additional agent for treating interstitial cystitis are either used or administered separately in time and/or in mode of administration or use (i.e. different routes of administration or use) or they are administered or for use together in the same pharmaceutical preparation and/or at the same time, which may depend, for example on the identity of the agent.

It is an embodiment that the CB2 target agent local anaesthetic and the additional agent for treating interstitial cystitis are used or administered separately in time and/or in mode of administration or use.

In another embodiment, the CB2 target agent local anaesthetic and the additional agent for treating interstitial cystitis are administered or for use contemporaneously. As used herein, contemporaneous administration or use of two substances to a subject means providing the CB2 target agent local anaesthetic and the additional agent for treating interstitial cystitis so that the pharmacological effects of the CB2 target agent local anaesthetic and the additional agent for treating interstitial cystitis are present in the subject at the same time. The exact details of the administration or use will depend on the pharmacokinetics of the CB2 target agent local anaesthetic and the additional agent for treating interstitial cystitis in the presence of each other, and can include administering or use of the CB2 target agent local anaesthetic and the additional agent for treating interstitial cystitis within a few hours of each other, or even administering or use of the CB2 target agent local anaesthetic and the additional agent for treating interstitial cystitis within 24 hours, or 48 hours or greater of administration or use of the other, if the pharmacokinetics are suitable. In one embodiment, contemporaneous administration or use comprises administering or use of the CB2 target agent local anaesthetic daily for a desired period of time and administering or use of the additional agent for treating interstitial cystitis (such as DMSO or MSM) as one or more cycles over a desired period of time, wherein administration or use of the CB2 target agent local anaesthetic and additional agent for treating interstitial cystitis may or may not commence at the same time and may or may not finish at the same time. Design of suitable dosing regimens is routine for one skilled in the art.

In another embodiment of the present application, the CB2 target agent local anaesthetic and the additional agent for treating interstitial cystitis are administered to a subject or for use in a non-contemporaneous fashion.

In a further embodiment of the present application, the CB2 target agent local anaesthetic and the additional agent for treating interstitial cystitis are administered to the subject or for use in a contemporaneous fashion followed by, or alternating with, administration or use in a non-contemporaneous fashion, for example, administration or use of the CB2 target agent local anaesthetic and the additional agent for treating interstitial cystitis in a contemporaneous fashion followed by administration or use of the CB2 target agent local anaesthetic to the subject without administration of the additional agent for treating interstitial cystitis.

The dosage of the CB2 target agent local anaesthetic and optionally the additional agent for treating interstitial cystitis varies depending on many factors such as the pharmacodynamic properties thereof, the mode of administration or use, the age, sex, health and/or weight of the subject, the nature and extent of the symptoms, the frequency of the treatment and the type of concurrent treatment, if any, and the clearance rate in the subject to be treated. One of skill in the art can determine the appropriate dosage based on the above factors. As a representative example, oral dosages of the CB2 target agent local anaesthetic may range between about 1 mg per day to about 1000 mg per day for a human adult. In an embodiment of the present application, the CB2 target agent local anaesthetic (e.g. beta-C) is formulated for oral administration or use and the CB2 target agent local anaesthetic is, for example in the form of capsules containing 0.25, 0.5, 0.75, 1.0, 5.0, 10.0, 20.0, 25.0, 30.0, 40.0, 50.0, 60.0, 70.0, 75.0, 80.0, 90.0, 100.0, 150, 200, 250, 300, 350, 400, 450, 500, 550, 600, 650, 700, 750, 800, 850, 900, 950 or 1000 mg of CB2 target agent local anaesthetic (e.g. beta-C) per capsule. In another embodiment, the capsules contain 25 mg of the CB2 target agent local anaesthetic (e.g. beta-C) per capsule. As a representative example, oral dosages of the methylsulfonylmethane (MSM) may range up to about 4000 mg per day for a human adult. In an embodiment of the present application, the oral dosage of the MSM is from about 1500 mg per day to about 2000 mg per day. In another embodiment of the present application, the MSM is formulated for oral administration or use and the MSM is, for example in the form of capsules containing 50, 100, 150, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950 or 2000 mg of MSM per capsule. The CB2 target agent local anaesthetic and optionally the additional agent for treating interstitial cystitis may be administered or for use initially in a suitable dosage that may optionally be adjusted as required, depending on the clinical response.

The following non-limiting examples are illustrative of the present application:

EXAMPLES

Example 1: Local and Systemic Inflammation Animal Models with Resultant Bladder Inflammation I. Materials and Methods
(a) Animal Models
Animals:

Female CD-1 and BALB/c mice (20 to 40 g) were obtained from Charles River Laboratories, Inc. (Wilmington, Mass., USA) and used for the experiments after a 1 week acclimatization period. All experimental procedures were performed according to the Canadian Council for Animal Care guidelines, and were approved by the Dalhousie University Committee on Laboratory Animals. The animals were housed in the Carlton Animal Care Facility of the Faculty of Medicine at Dalhousie University, Halifax, NS, Canada. The mice used in this study were provided with water and rodent chow ad libitum under standard 12-hour light/dark rhythmic conditions. Two animal IC models were used: the systemic (endotoxemia-induced) bladder inflammation model and the local (endotoxin-induced) bladder inflammation model.

Systemic Bladder Inflammation Model:

The animals were anesthetized via pentobarbital administration (i.p.). Following anesthesia induction, 10 mg/kg lipopolysaccharide (LPS; synonym: endotoxin) was administered intraperitoneally to induce systemic inflammation (=endotoxemia). Following the LPS injection (t=0 min), animals received therapies depending on the experimental group (t=15 min). After the treatment, the animals were placed on a heating pad and closely monitored for depth of anesthetic, breathing and general comfort. Two hours after treatment animals were prepared for IVM as described hereinbelow. The groups of mice were as follows: (1) saline-injected control group, (2) LPS-injected experimental group, and (3) LPS and 100 mg/kg Beta-C-injected treatment group.

Local Bladder Inflammation Model:

Animals were anesthetized via pentobarbital administration (i.p.). Thereafter, a P10 catheter was gently inserted into urethra. Flexible catheters were used as they are less likely to cause urethral trauma. The bladder was then manually drained by using Credo's maneuver, which involves applying gentle pressure on the bladder to remove bladder contents. After, LPS solution (100 μg/ml) was slowly instilled for 30 minutes[25]. To avoid backflow or leakage, the catheter was clamped after the intravesical instillation. Upon the expiration of the LPS instillation period, the LPS solution was removed from the bladder and replaced by saline or drug instillation, depending on the experimental group. The groups of mice were as follows: (1) control group with saline instillation, (2) LPS group with saline instillation, (3) LPS group with Beta-C and DMSO (40%) instillation, and (4) LPS group with DMSO (40%) instillation. In group (3), Beta-C was dissolved in DMSO prior to administration, and DMSO and Beta-C were administered as one single instillation at the same time.

(b) Intravital Microscopy of the Bladder

Anesthesia was maintained with repeated IP injections of 5 mg/kg pentobarbital while the depth of anesthesia was continuously monitored by clinical examination (return of the pedal withdrawal reflex). A laparotomy was performed to prepare the bladder for intravital microscopy (IVM). The bladder was then gently exposed with pre-wetted (warm saline) cotton tip applicators and positioned at a slight angle. A small cover slip was placed on top of the bladder to allow microscopy observation. To avoid breathing artifacts during intravital microscopy, abdominal fat and muscles were kept away from the bladder via a metal arm that applies gentle pressure to a heated and moisturized cotton sponge on the upper abdominal area to prevent significant movement due to diaphragm activity such as breathing. While the abdominal incision was kept as small as possible, any areas of abdominal region not being subjected to examination were covered with gauze, partly immersed in and continuously super-hydrated with normal saline solution maintained at physiological temperature to avoid dehydration and exposure to ambient air. To visualize leukocyte-endothelial interactions, 0.05% Rhodamin-6G solution was administered i.v. via tail vein injection and 5% FITC-albumin solution i.v. was used to facilitate clearer evaluation of the capillary bed. Following focus setting, five video sequences (30 sec.) of random fields of the capillaries within the bladder wall were recorded using a computerized imaging system. The video sequences were then analyzed according to established protocols.

(c) Statistical Analysis

Results were analyzed using the software Prism 6 (GraphPad Software, La Jolla, Calif., USA). All data are expressed as means±standard deviation (SD). Following confirmation of normal distribution by Kolmogorov-Smirnov test, groups were tested for significance using one-way analysis of variance (ANOVA) with a Dunnett's post hoc test. Significance was considered at $p<0.05$.

II. Results (a) Systemic Bladder Inflammation Model

Leukocyte Adherence:

FIG. 1 shows the results of leukocyte adhesion in bladder venules of female CD-1 mice for healthy controls (CON; n=9), untreated LPS-induced cystitis (LPS; n=9), and LPS-induced cystitis treated with Beta-C (Beta-C, n=7), a CB2 agonist. Data presented as mean±SD. *$p<0.05$ vs. CON. #$p<0.05$ vs LPS. As shown in FIG. 1, low baseline level of leukocyte adherence was observed in control animals. A significant increase in the number of adherent leukocytes was seen in endotoxin challenged animals compared to control animals. As can be seen from FIG. 1, Beta-C treatment significantly decreased the number of adhering leukocytes.

Figure 2:
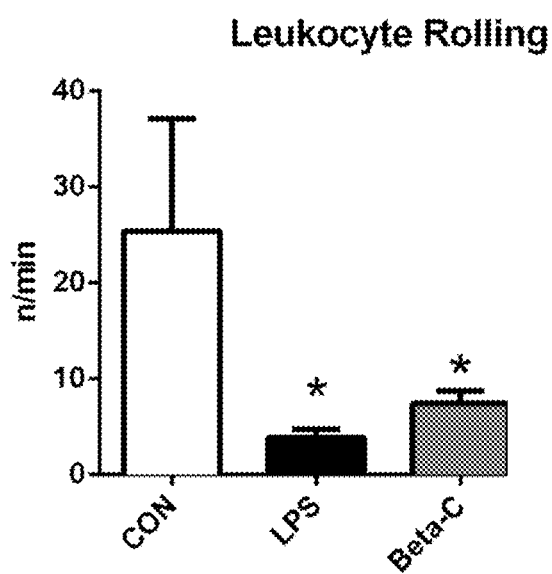
FIG. 2 is a plot showing leukocyte rolling (n/min) in bladder venules of female CD-1 mice for a lipopolysaccharide (LPS)-induced cystitis model treated with beta-caryophyllene (Beta-C) in comparison to healthy controls (CON) and untreated LPS-induced cystitis (LPS). Data presented as mean±SD.

Leukocyte Rolling:

FIG. 2 shows the results of leukocyte rolling in bladder venules of female CD-1 mice for healthy controls (CON; n=9), untreated LPS-induced cystitis (LPS; n=9), and LPS-induced cystitis treated with Beta-C (Beta-C, n=7), a CB2 agonist. Data presented as mean±SD. *$p<0.05$ vs. CON. As shown in FIG. 2, the healthy control group was associated with a base level of leukocyte rolling. LPS administration caused a significant decrease in the number of rolling leukocytes compared to control animals. Beta-C treatment group showed a positive trend but did not significantly alter the number of rolling leukocytes compared to endotoxemia group.

Figure 3:
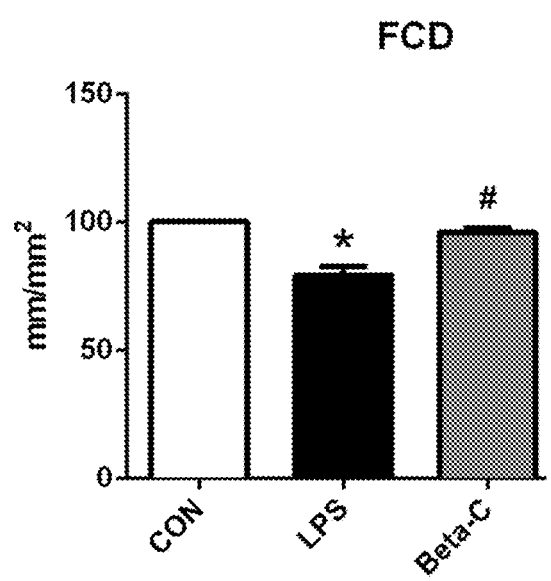
FIG. 3 is a plot showing capillary perfusion (mm/mm$^2$) quantified through functional capillary density (FCD) within the capillaries of female CD-1 mice for a lipopolysaccharide (LPS)-induced cystitis model treated with beta-caryophyllene (Beta-C) in comparison to healthy controls (CON) and untreated LPS-induced cystitis (LPS). Data presented as mean±SD.
Figure 4:
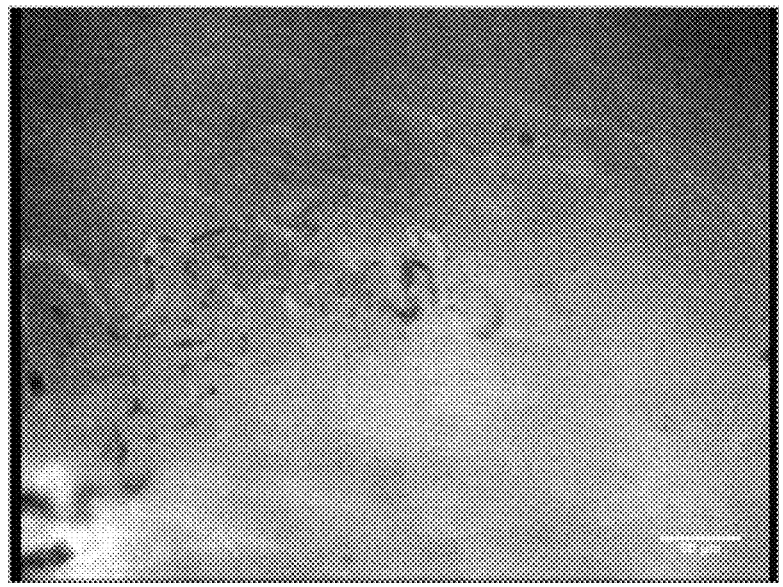
FIG. 4 is a micrograph of bladder capillaries of a female CD-1 mouse with LPS-induced interstitial cystitis showing poorly perfused and reduced capillary bed size. Scale bar shows 50 µm.
Figure 5:
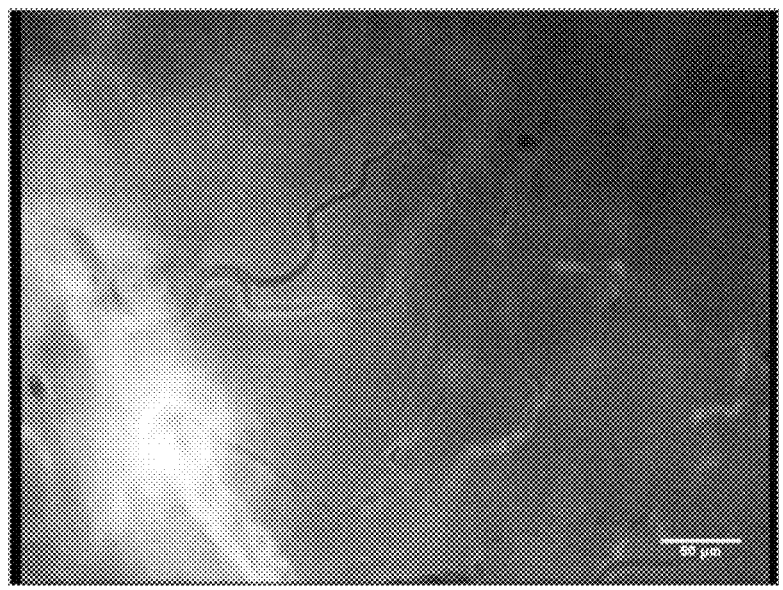
FIG. 5 is a micrograph of bladder capillaries of a healthy control female CD-1 mouse, well perfused with good spread of capillary bed. Scale bar shows 50 µm.

Functional Capillary Density:

FIG. 3 shows the results of capillary perfusion quantified through functional capillary density (FCD) within the capillaries of female CD-1 mice for healthy controls (CON; n=9), untreated LPS-induced cystitis (LPS; n=9), and LPS-induced cystitis treated with Beta-C (Beta-C, n=7), a CB2 agonist. Data presented as mean±SD. *$p<0.05$ vs. CON. #$p<0.05$ vs LPS. As can also be seen in FIGS. 4-5, there was a significant reduction in the number of functional capillaries in the bladder microcirculation following endotoxin challenge (FIG. 4) compared to healthy control group (FIG. 5). Administration of Beta-C restored perfusion to levels observed in healthy control animals.

(b) Local Bladder Inflammation Model

Figure 6:
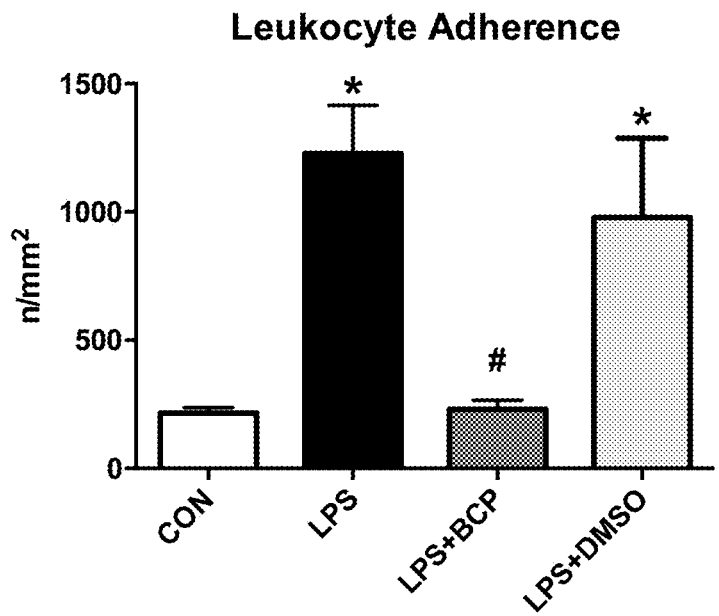
FIG. 6 is a plot showing leukocyte adhesion (n/mm$^2$) in bladder venules of female BALB/c mice for a lipopolysaccharide (LPS)-induced cystitis model treated with combination Beta-C/DMSO40% instillation (LPS+BCP) in comparison to treatment with DMSO40% installation alone (LPS+DMSO), healthy controls (CON) and untreated LPS-induced cystitis (LPS). Data presented as mean±SD.

Leukocyte Adherence: FIG. 6 shows the results of leukocyte adhesion in bladder venules of female BALB/c mice for healthy controls (CON; n=5), untreated LPS-induced cystitis (LPS; n=5), LPS-induced cystitis treated with BCP/DMSO40% instillation (LPS+BCP; n=3), and LPS-induced cystitis treated with DMSO40% installation (LPS+DMSO, n=2). Data presented as mean±SD. *$p<0.05$ vs. CON. #$p<0.05$ vs LPS. As shown in FIG. 6, a low baseline level of leukocyte adherence was observed in control animals. A significant increase in the number of adherent leukocytes was seen in endotoxin challenged animals compared to control animals. Beta-C+DMSO treatment significantly decreased the number of adhering leukocytes. In contrast, DMSO treatment alone did not significantly decrease leukocyte adherence.

Figure 7:
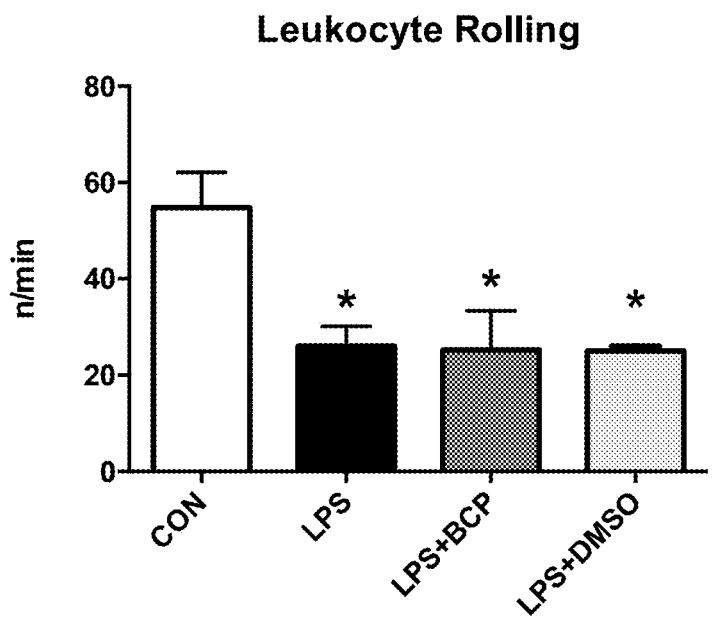
FIG. 7 is a plot showing leukocyte rolling (n/min) in bladder venules of female BALB/c mice for a lipopolysaccharide (LPS)-induced cystitis model treated with combination Beta-C/DMSO40% instillation (LPS+BCP) in comparison to treatment with DMSO40% installation alone (LPS+DMSO), healthy controls (CON) and untreated LPS-induced cystitis (LPS). Data presented as mean±SD.

Leukocyte Rolling:

FIG. 7 shows the results of leukocyte rolling in bladder venules of female BALB/c mice for healthy controls (CON; n=5), untreated LPS-induced cystitis (LPS; n=5), LPS-induced cystitis treated with BCP/DMSO40% instillation (LPS+BCP; n=3), and LPS-induced cystitis treated with DMSO40% (LPS+DMSO, n=2). Data presented as mean±SD. *$p<0.05$ vs. CON. As shown in FIG. 7, the healthy control group was associated with a basal level of leukocyte rolling. LPS administration caused a significant decrease in the number of rolling leukocytes compared to control animals. Beta-C treatment with DMSO or DMSO alone did not show any significant difference when compared to the endotoxemia group in this model.

Figure 8:
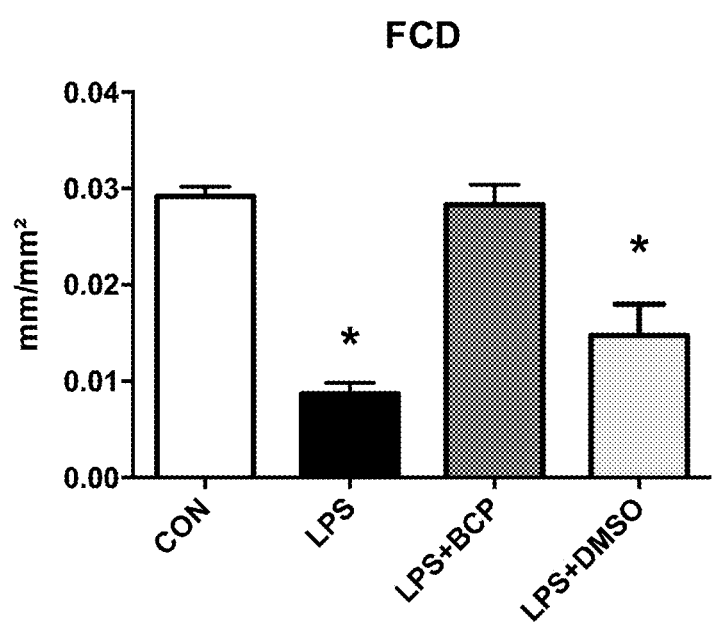
FIG. 8 is a plot showing capillary perfusion (mm/mm$^2$) quantified through functional capillary density (FCD) within the capillaries of female BALB/c mice for a lipopolysaccharide (LPS)-induced cystitis model treated with combination Beta-C/DMSO40% instillation (LPS+BCP) in comparison to treatment with DMSO40% installation alone (LPS+DMSO), healthy controls (CON) and untreated LPS-induced cystitis (LPS). Data presented as mean±SD.

Functional Capillary Density:

FIG. 8 shows the results of capillary perfusion quantified through functional capillary density (FCD) within the capillaries of female BALB/c mice for healthy controls (CON; n=5), untreated LPS-induced cystitis (LPS; n=5), LPS-induced cystitis treated with BCP/DMSO40% instillation (LPS+BCP; n=3), and LPS-induced cystitis treated with DMSO40% (LPS+DMSO, n=2). Data presented as mean±SD. *$p<0.05$ vs. CON. #$p<0.05$ vs LPS. As can be seen in FIG. 8 there was a significant reduction in the number of functional capillaries in the bladder microcirculation following endotoxin challenge compared to control group. Administration of Beta-C with DMSO restored perfusion to levels observed in healthy control animals. In contrast, while treatment with DMSO alone did improve perfusion, it did not return perfusion to the levels observed in healthy control animals.

III. Discussion

The local and systemic inflammation models with resultant bladder inflammation provide an experimental model of inflammation and bladder dysfunction and pain. The data in FIGS. 1-3 and 6-8 showed the following: 1) a decrease in leukocyte-endothelial adhesion following LPS challenge in the Beta-C treatment group; and 2) a significant improvement in capillary perfusion of the bladder, following LPS challenge in the Beta-C treatment group; but 3) no significant change in leukocyte rolling in the Beta-C treatment group potentially for the reasons discussed in greater detail hereinbelow.

The findings in the current study not only show the attenuation of the inflammatory response in cystitis through the modulation of the CB2 receptor they also provide new data identifying a role for certain CB2 ligands, such as the terpenoid Beta-C, that act via multiple targets; both cannabinoid receptor and non-cannabinoid receptor, to reduce not only inflammation but also pain and produce relief via local anesthesia. Additionally, the results of the present studies show that combination therapies such as DMSO and CB2 orthosteric agonists (e.g. Beta-C) may be advantageous over existing therapies such as DMSO alone.

Urothelial dysfunction results in upregulation of cytokine production, and mast cell activation. Current evidence from experimental studies has suggested that bladder mast cell activation plays a central role in the pathophysiology of IC[26]. Furthermore, mast cells are said to be involved in inflammation because they secrete various cytokines like Interleukin (IL)-6, tumour necrosis factor-alpha (TNF-α)[27]. Additionally, mast cells themselves produce and regulate the expression of cellular adhesion molecules (CAM), which are molecules that mediate the leukocyte-endothelial interactions, necessary for initiation of inflammation[28] especially, endothelial cell ICAM-1 (intracellular CAM-1) and vascular cell adhesion molecule-1 (VCAM-1). A study investigating the presence of ICAM-1 and other molecules involved in leukocyte-endothelial adhesion in bladder biopsies from patients with IC showed the bladder tissue of IC patients had expression of various CAMs[29]. Furthermore, it has been shown that mast cells require toll-like receptor 4 (TLR-4) for activation in response to LPS challenge in LPS induced models of inflammation[30]. While not wishing to be limited by theory, this suggests that the process of expression and regulation of ICAM-1 by activated mast cells resulting in an increase in leukocyte adhesion and augmentation of the inflammatory response is occurring within the model of LPS-induced IC used in the present studies. During inflammation, when the number of adherent leukocytes increases it is expected to see a decrease in leukocyte rolling, which is observed across the groups in the present study. However, the administration of Beta-C, with the associated reduction in leukocyte adhesion did not restore leukocyte rolling to comparable levels seen in the control group. One reason for this may be that the timing of the observation was too early to notice a significant shift in rolling numbers. However, while not wishing to be limited by theory, another possible explanation is that Beta-C continues to suppress the recruitment of leukocytes, which may explain the low numbers of rolling leukocytes observed following Beta-C treatment.

Microvascular perfusion is a useful indicator of the general physiological status of the vasculature. The regulation of capillary perfusion is achieved through the interplay of neuroendocrine, paracrine, and mechanosensory pathways.[31] However, during systemic inflammation a disruption in this process is noticed due to various factors such as decreased deformability of red blood cells, increased blood viscosity, and increase in aggregability of activated leukocytes because of an up regulation of adhesion molecules[32]. While not wishing to be limited by theory, it is believed that these mechanisms account for the FCD changes observed in the groups. Furthermore, findings have showed that blockade of TLR-4 in a rat endotoxemia model increases intestinal microcirculatory perfusion[33]. While not wishing to be limited by theory this suggests LPS mediated activation of TLR-4 pathway plays a role in capillary perfusion. For example, while not wishing to be limited by theory, Beta-C's direct or indirect inhibition of NF-κB which is involved in increasing release of pro-inflammatory cytokines and adhesion molecules[34] may have led to the improvement in FCD observed in the present study therefore compounds exhibiting similar activity may also be useful for treatment of this condition. The presence of significant improvement within the vascular perfusion data in the Beta-C treatment groups, despite the excessive immunoactivation posed by the LPS challenge, while not wishing to be limited by theory, suggests a strong role of CB2-related immunomodulation in experimental IC.

In a clinical study, it was observed that IL-6 and TNF-α, pro-inflammatory cytokines, released by mast cells are two of the chief cytokines found in high concentration in the serum of patients with IC, and they can be developed as biomarkers for IC[35]. While not wishing to be limited by theory, this marked increase in IL-6 and TNF-α may be in part due to the role of mast cells in IC. In line with these findings, a number of studies have also reported the suppression of pro-inflammatory cytokines, specifically TNF-α, through CB2 receptor activation in LPS treated rodent neuroglia or LPS induced endotoxemia[36]. While not wishing to be limited by theory, this may have led to the observed therapeutic effects of Beta-C in the present studies and therefore compounds exhibiting similar activity may also be useful for treatment of IC.

In summary, the data suggests that CB2 receptor agonists having additional local anaesthetic actions such as Beta-C may be useful in reducing both inflammation and pain in IC and that when these agents are additionally co-administered with an existing therapy for IC, such as DMSO therapy, the efficacy of such a combination therapy for IC may be advantageous.

Example 2: Additional Studies Using Local and Systemic Inflammation Animal Models with Resultant Bladder Inflammation I. Materials and Methods
Animals:
Female BALB/c mice (6 weeks old on arrival, 20-30 g in weight) were obtained from Charles River Laboratories, Inc. (Wilmington, Mass., USA) and used for the experiments after a 1-week acclimatization period. All experimental procedures were performed according to the Canadian Council for Animal Care guidelines and were approved by the Dalhousie University Committee on Laboratory Animals. The animals were housed in the Carlton Animal Care Facility of the Faculty of Medicine at Dalhousie University, Halifax, NS, Canada. The mice used in this study were provided with water and rodent chow ad libitum under standard 12-hour light/dark rhythmic conditions.

Local Bladder Inflammation Model:
Animals were anesthetized via pentobarbital administration (i.p.). Laparotomy was then performed to gain access to the bladder and to have a visual confirmation of bladder instillation success. Once the bladder was exposed from the surrounding tissue and organs, it was manually drained by gentle pressure (similar to Credo's maneuver, which involves applying gentle pressure on the bladder to remove bladder contents). This was then followed by an insertion of a P10 catheter into the urethra. Flexible catheters were used as they are less likely to cause urethral trauma. LPS solution (150 µg/ml) was slowly instilled and held in the bladder for 30 minutes. The animal was then rotated on the heating pad at a halfway point to ensure that all sides of bladder were equally exposed to LPS. To avoid backflow or leakage, the catheter was clamped after the intravesical instillation. Upon the expiration of the LPS instillation period, the LPS solution was removed from the bladder and replaced by saline or drug instillation (as described hereinabove in Example 1), depending on the experimental group.

Intravital Microscopy of the Bladder:

The same anesthetized animals from above were maintained with repeated IP injections of 5 mg/kg pentobarbital while the depth of anesthesia was continuously monitored by clinical examination (return of the pedal withdrawal reflex). The bladder was gently exposed again with pre-wetted (warm saline) cotton tip applicators and positioned at a slight angle. A small cover slip was placed on top of the bladder to allow microscopy observation. To avoid breathing artifacts during intravital microscopy, abdominal fat and muscles were kept away from the bladder via a metal arm that applies gentle pressure to a heated and moisturized cotton sponge on the upper abdominal area to prevent significant movement due to diaphragm activity such as breathing. While the abdominal incision was kept as small as possible, any areas of abdominal region not being subjected to examination were covered with gauze, partly immersed in and continuously super-hydrated with normal saline solution maintained at physiological temperature to avoid dehydration and exposure to ambient air. To visualize leukocyte-endothelial interactions, 0.05% Rhodamin-6G solution was administered i.v. via tail vein injection and 5% FITC-albumin solution i.v. was used to facilitate clearer evaluation of the capillary bed. Following focus setting, five video sequences (30 sec.) of random fields of the capillaries within the bladder wall were recorded using a computerized imaging system. The video sequences were then analyzed according to established protocols.

Statistical Analysis:

Results were analyzed using the software Prism 6 (GraphPad Software, La Jolla, Calif., USA). All data are expressed as means±standard deviation (SD). Following confirmation of normal distribution by Kolmogorov-Smirnov test, groups were tested for significance using one-way analysis of variance (ANOVA) with a Dunnett's post hoc test. Significance was considered at $p<0.05$.

II. Results and Discussion

BCP Instillation Decreases Leukocyte Adhesion in Experimental Cystitis.

Figure 9:
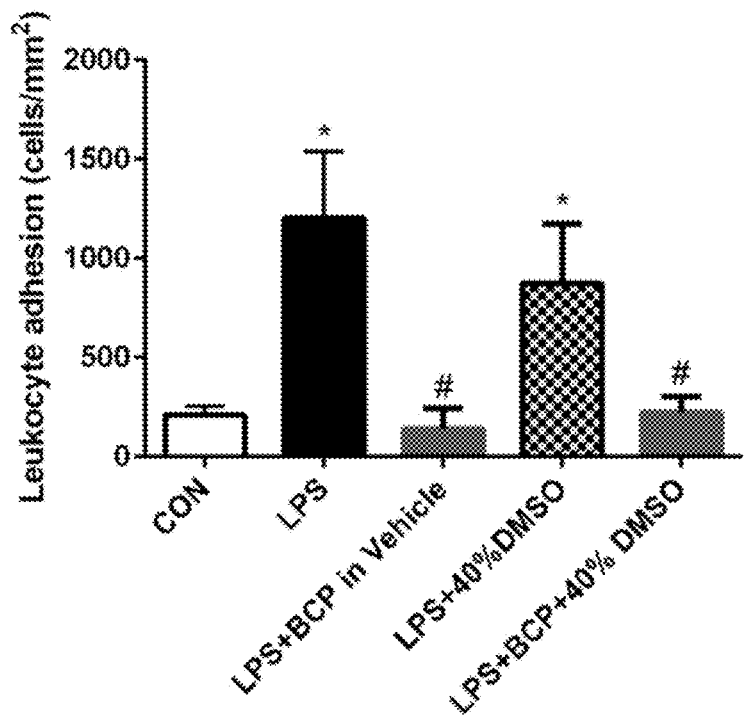
FIG. 9 is a plot showing leukocyte adhesion (cells/mm$^2$) in bladder venules of female BALB/c mice for a lipopolysaccharide (LPS)-induced cystitis model treated with beta-caryophyllene (BCP), 40% DMSO, or a combination of BCP and 40% DMSO in comparison to healthy controls (CON) and untreated LPS-induced cystitis (LPS). Data presented as mean±SD.

FIG. 9 shows the results of leukocyte adhesion in bladder venules of female BALB/c mice for healthy controls (CON; n=6), untreated LPS-induced cystitis (LPS; n=8), LPS-induced cystitis treated with BCP (100 mg/kg) in vehicle instillation (LPS+BCP in vehicle; n=6), LPS-induced cystitis treated with a 40% DMSO instillation (LPS+DMSO, n=5) and LPS-induced cystitis treated with BCP (100 mg/kg) in a 40% DMSO instillation (LPS+BCP+40% DMSO, n=5). Data presented as mean±SD. *$p<0.05$ vs. CON. #$p<0.05$ vs LPS. As shown in FIG. 9, a low baseline level of leukocyte adherence was observed in control animals. A significant increase in the number of adherent leukocytes was seen in endotoxin challenged animals compared to control animals. Beta-C (100 mg/kg) treatment significantly decreased the number of adhering leukocytes back to the level of healthy control animals. In contrast, the 40% DMSO treatment retained a high level of activated leukocytes in this model.

BCP Instillation Restores Leukocyte Rolling in Experimental Cystitis.

Figure 10:
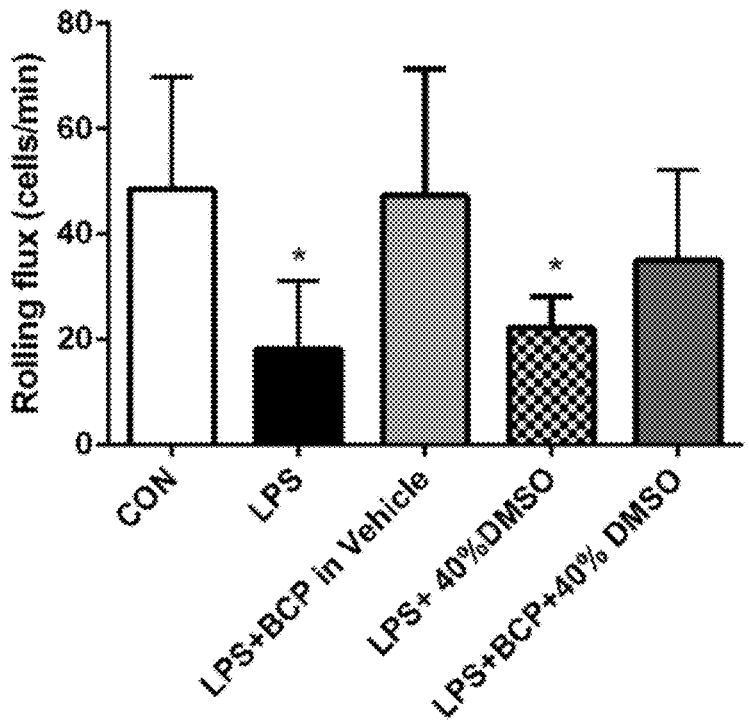
FIG. 10 is a plot showing leukocyte rolling (cells/min) in bladder venules of female BALB/c mice for a lipopolysaccharide (LPS)-induced cystitis model treated with beta-caryophyllene (BCP), 40% DMSO, or a combination of BCP and 40% DMSO in comparison to healthy controls (CON) and untreated LPS-induced cystitis (LPS). Data presented as mean±SD.

FIG. 10 shows the results of leukocyte rolling in bladder venules of female BALB/c mice healthy controls (CON; n=6), untreated LPS-induced cystitis (LPS; n=8), LPS-induced cystitis treated with BCP (100 mg/kg) in vehicle instillation (LPS+BCP in vehicle; n=6), LPS-induced cystitis treated with a 40% DMSO instillation (LPS+40% DMSO, n=5) and LPS-induced cystitis treated with BCP (100 mg/kg) in a 40% DMSO instillation (LPS+BCP+40% DMSO, n=5). Data presented as mean±SD. *$p<0.05$ vs. CON. As shown in FIG. 10, the healthy control group was associated with a basal level of leukocyte rolling. LPS administration caused a significant decrease in the number of rolling leukocytes compared to control animals. BCP treatment in vehicle restored the level of leukocyte levels to that of control animals. DMSO administration did not improve leukocyte rolling and did not show any significant difference when compared to the endotoxemia group (LPS) in this model. Combining BCP and DMSO administration also improved the rolling flux number, when compared to the untreated group.

BCP Instillation Restores Functional Capillary Density in Experimental Cystitis.

Figure 11:
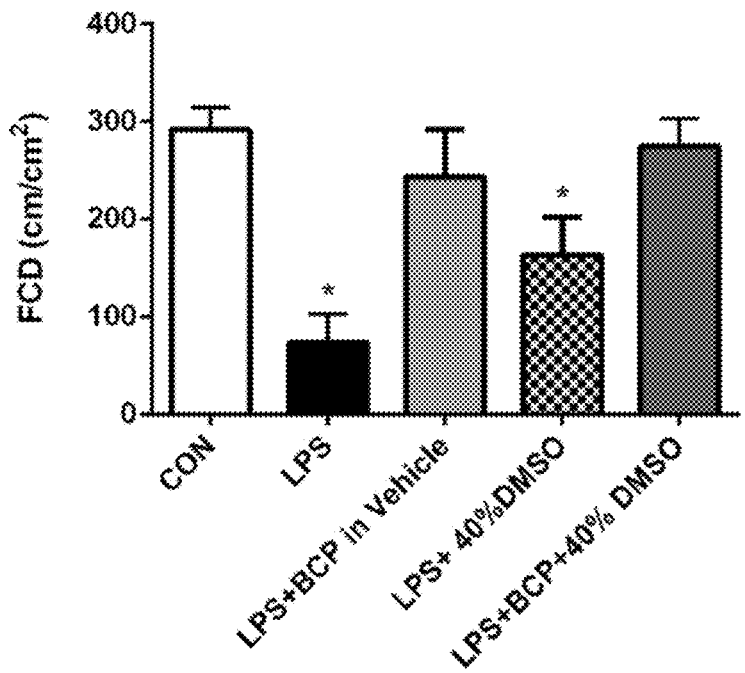
FIG. 11 is a plot showing capillary perfusion (cm/cm$^2$) quantified through functional capillary density (FCD) within the capillaries of female BALB/c mice for a lipopolysaccharide (LPS)-induced cystitis model treated with beta-caryophyllene (BCP), 40% DMSO, or a combination of BCP and 40% DMSO in comparison to healthy controls (CON) and untreated LPS-induced cystitis (LPS). Data presented as mean±SD.

FIG. 11 shows the results of capillary perfusion quantified through functional capillary density (FCD) within the capillaries of female BALB/c mice for healthy controls (CON; n=6), untreated LPS-induced cystitis (LPS; n=8), LPS-induced cystitis treated with BCP (100 mg/kg) in vehicle instillation (LPS+BCP in vehicle; n=6), LPS-induced cystitis treated with a 40% DMSO instillation (LPS+40% DMSO, n=5) and LPS-induced cystitis treated with BCP (100 mg/kg) in 40% DMSO instillation (LPS+BCP+40% DMSO, n=5). Data are presented as mean±SD. *$p<0.05$ vs. CON. As can be seen in FIG. 11, there was a significant reduction in the number of functional capillaries in the bladder microcirculation following endotoxin (LPS) challenge compared to the control group. Administration of BCP in vehicle, as well as BCP in 40% DMSO restored perfusion to levels observed in healthy control animals. In contrast, while treatment with DMSO alone did improve perfusion, it did not return perfusion to the levels observed in healthy control animals.

BCP in DMSO Instillation Reduces Leukocyte Adherence in Experimental Cystitis.

Figure 12:
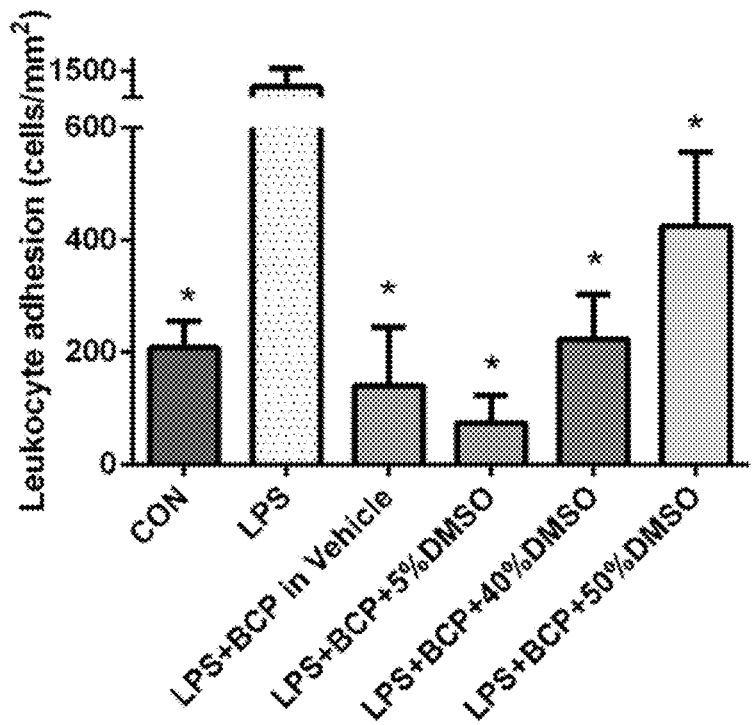
FIG. 12 is a plot showing leukocyte adhesion (cells/mm$^2$) in bladder venules of female BALB/c mice for a lipopolysaccharide (LPS)-induced cystitis model treated with beta-caryophyllene (BCP) or combinations of BCP and 5% DMSO, 40% DMSO or 50% DMSO in comparison to healthy controls (CON) and untreated LPS-induced cystitis (LPS). Data presented as mean±SD.

FIG. 12 shows the results of leukocyte adhesion in bladder venules of female BALB/c mice for healthy controls (CON; n=6), untreated LPS-induced cystitis (LPS; n=8), LPS-induced cystitis treated with BCP (100 mg/kg) in vehicle (LPS+BCP in Vehicle; n=6), LPS-induced cystitis treated with BCP (100 mg/kg) in a 5% DMSO instillation (LPS+BCP+5% DMSO; n=4), LPS-induced cystitis treated with BCP (100 mg/kg) in a 40% DMSO instillation (LPS+BCP+40% DMSO, n=5) and LPS-induced cystitis treated with BCP (100 mg/kg) in a 50% DMSO instillation (LPS+BCP+50% DMSO; n=3). Data are presented as mean±SD. *$p<0.05$ vs. LPS+BCP+50% DMSO. As shown in FIG. 12, increased leukocyte adherence was observed in animals with untreated LPS-induced cystitis. A significant decrease in the number of adherent leukocytes was seen in all animal groups treated with BCP, including BCP in vehicle treatment which produced a decrease in leukocyte adherence comparable to groups instilled with various levels of DMSO (a standard current clinical treatment). BCP in 5% DMSO instillation yielded the lowest overall values for leukocyte adherence.

BCP in DMSO Instillation Improves Functional Capillary Density in Experimental Cystitis.

Figure 13:
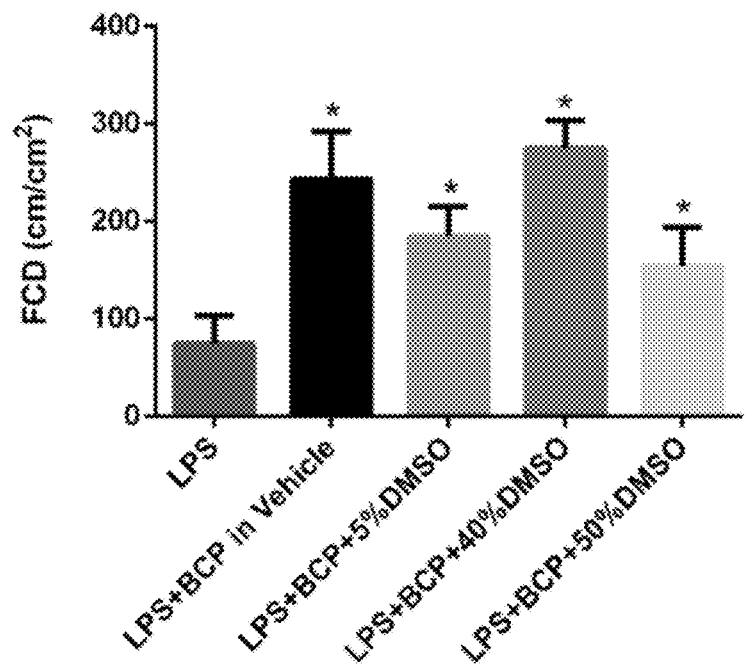
FIG. 13 is a plot showing capillary perfusion (cm/cm$^2$) quantified through functional capillary density (FCD) within the capillaries of female BALB/c mice for a lipopolysaccharide (LPS)-induced cystitis model treated with beta-caryophyllene (BCP) or combinations of BCP and 5% DMSO, 40% DMSO or 50% DMSO in comparison to untreated LPS-induced cystitis (LPS). Data presented as mean±SD.

FIG. 13 shows the results of capillary perfusion quantified through functional capillary density (FCD) within the capillaries of female BALB/c mice with untreated LPS-induced cystitis (LPS; n=8), LPS-induced cystitis treated with BCP (100 mg/kg) in vehicle (LPS+BCP in Vehicle; n=6), LPS-induced cystitis treated with BCP (100 mg/kg) in 5% DMSO instillation (LPS+BCP+5% DMSO; n=4), LPS-induced cystitis treated with BCP (100 mg/kg) in 40% DMSO instillation (LPS+BCP+40% DMSO, n=5) and LPS-induced cystitis treated with BCP (100 mg/kg) in a 50% DMSO instillation (LPS+BCP+50% DMSO; n=3). Data are presented as mean±SD. *p<0.05 vs. LPS. As shown in FIG. 13, a high level of capillary dysfunction was observed in animals with untreated LPS-induced cystitis. A significant improvement in capillary perfusion of the bladder was seen in all animal groups with experimental cystitis treated with BCP. Treatment with BCP in vehicle produced a significant improvement in FCD, comparable to groups with experimental cystitis and only treated with various levels of DMSO instillation. Beta-C in vehicle and Beta-C in 40% DMSO instillation, yielded the highest overall values for FCD.

Example 3: Additional Studies Using Local Bladder Inflammation Model (a) Intravesical Administration of Beta-C with Methylsulfonylmethane (MSM)

Studies are carried out to investigate intravesical administration of a combination of Beta-C and MSM.

The groups are as follows:
1. Control
2. LPS (local)
3. LPS (local)+Beta-C (intravesical)
4. LPS (local)+MSM (intravesical)
5. LPS (local)+MSM (intravesical)+Beta-C (intravesical)

LPS (local) and Beta-C (intravesical) are provided as detailed hereinabove in Example 1. MSM is provided similar to as detailed hereinabove in Example 1 for DMSO. Leukocyte adherence, leukocyte rolling and functional capillary density are measured using the techniques described in Example 1. The combination treatment of MSM and Beta-C has greater efficacy in leukocyte adherence and functional capillary density than Beta-C or MSM alone.

(b) Oral Beta-C in Combination with Intravesical DMSO or MSM

Oral Beta-C is investigated as an alternative route of administration. This route of administration offers the potential for interval treatment along with intravesical DMSO or MSM therapy. In a clinical context, interval treatment may allow for oral treatments (i.e. less invasive as could be provided outside of a clinic or hospital) with a CB2 target agent local anaesthetic e.g. beta-C between intravesical treatments which would typically be administered at a clinic or hospital.

The groups are as follows:
1. Control
2. LPS (local)
3. LPS (local)+Beta-C (oral; gavage)
4. LPS (local)+DMSO (intravesical)
5. LPS (local)+MSM (intravesical)
6. LPS (local)+DMSO (intravesical)+Beta-C (oral; gavage)
7. LPS (local)+MSM (intravesical)+Beta-C (oral; gavage)

In the oral gavage group, the mice are treated with 10 mg/kg beta-C by gavage 60 minutes prior to LPS exposure. LPS (local) and DMSO (intravesical) are provided as detailed hereinabove in Example 1. MSM is provided similar to as detailed hereinabove in Example 1 for DMSO. Leukocyte adherence, leukocyte rolling and functional capillary density are measured using the techniques described in Example 1. The combination treatment of DMSO or MSM and Beta-C has greater efficacy in leukocyte adherence and functional capillary density than Beta-C or DMSO or MSM alone.

(c) Oral Beta-C in Combination with Oral MSM

The combination of oral Beta-C and oral MSM is investigated as an alternative route of administration. This route of administration offers the potential for less invasive treatment as could be provided outside of a clinic or hospital.

The groups are as follows:
1. Control
2. LPS (local)
3. LPS (local)+Beta-C (oral; gavage)
4. LPS (local)+MSM (oral; gavage)
5. LPS (local)+MSM (oral; gavage)+Beta-C (oral; gavage)

In the Beta-C oral gavage group, the mice are treated with 10 mg/kg beta-C by gavage 60 minutes prior to LPS exposure. In MSM oral gavage group, the mice are treated with 100 mg/kg MSM by gavage 60 minutes prior to LPS exposure. In the Beta-C+MSM oral gavage group, the mice are treated with 10 mg/kg beta-C and 100 mg/kg MSM by gavage 60 minutes prior to LPS exposure. LPS (local) is provided as detailed hereinabove in Example 1. Leukocyte adherence, leukocyte rolling and functional capillary density are measured using the techniques described in Example 1. The combination treatment of MSM and Beta-C has greater efficacy in leukocyte adherence and functional capillary density than Beta-C or MSM alone.

(d) Local Anesthetic Effect of Beta-C

Studies are carried out to further investigate the local anesthetic effect of Beta-C alone or in combination with DMSO or MSM. The groups are:
1. Control
2. LPS
3. LPS+Beta-C (oral; gavage)
4. LPS+DMSO (intravesical)
5. LPS+MSM (intravesical)
6. LPS+DMSO (intravesical)+Beta-C (oral; gavage)
7. LPS+MSM (intravesical)+Beta-C (oral; gavage)

In the oral gavage group, the mice are treated with 10 mg/kg beta-C by gavage 60 minutes prior to LPS exposure. LPS (local) and DMSO (intravesical) are provided as detailed hereinabove in Example 1. MSM is provided similar to as detailed hereinabove in Example 1 for DMSO.

Behavioural pain assessment is carried out to evaluate the local analgesic effect of Beta-C following local LPS challenge to induce IC. A combination of oral and intravesical treatment is used.

Behavioural Pain Assessment:

A maximum value of 10 is used for each of the 2 parameters observed, that is eye closure and abnormal posture (rounded back and stretched posture) with an extra 10 when animals also show other parameters such as licking the abdomen (brief pain crisis). Thus, the maximum score is 30. The minimal score is 0 if no parameters are affected (no pain). The term brief pain crisis indicates tail hyperextension, abdominal retraction and backward withdrawal movements. Abnormal posture is scored as 0-normal posture, 5-occasionally rounded back or stretching, 7-almost rounded back or stretched position, and 10-rounded back and stretching. Eye closure is scored as 0-completely open eyes, 5-half-closed eyes and 10-eyes completely closed. The final pain score is a composite of the scores derived from 14 measurements, each with a maximum score of 30, at 15-minute intervals starting 30 minutes after induction of cystitis.

Example 4: Oral Beta-C Alone and in Combination with Intravesical MSM

I. Materials and Methods

Oral Beta-C was investigated as an alternative route of administration. This route of administration offers the potential for interval treatment, optionally along with intravesical DMSO or MSM therapy. In a clinical context, interval treatment may allow for oral treatments (i.e. less invasive as could be provided outside of a clinic or hospital) with a CB2 target agent local anaesthetic e.g. beta-C between intravesical treatments which would typically be administered at a clinic or hospital.

Animals and local bladder inflammation model were as described hereinabove in Example 2. The groups were as follows:

1. Healthy Animal Control
2. LPS (local)
3. LPS (local)+Beta-C (oral; gavage)
4. Healthy Animal Control+Beta-C (oral; gavage)
5. LPS (local)+MSM+Beta-C (oral; gavage)
6. LPS (local)+MSM (intravesical)+Beta-C (oral; gavage)

In the oral gavage groups, the mice were treated with 100 mg/kg beta-C or 100 mg/kg beta-C in 100 mg/kg methyl-sulfonylmethane (MSM) by gavage. In groups other than the Healthy Animal Control administered oral beta-C, the administration was 60 minutes prior to LPS exposure. LPS (local) was provided as detailed hereinabove in Example 2. Intravesical MSM was provided similar to as detailed hereinabove in Example 1 for DMSO. Leukocyte adherence, leukocyte rolling and functional capillary density were measured using the techniques as described hereinabove in Example 2. Results were assessed using the statistical methods described hereinabove in Example 2.

II. Results and Discussion

Oral BCP Administration Reduces Leukocyte Adherence in Experimental Cystitis.

Figure 14:
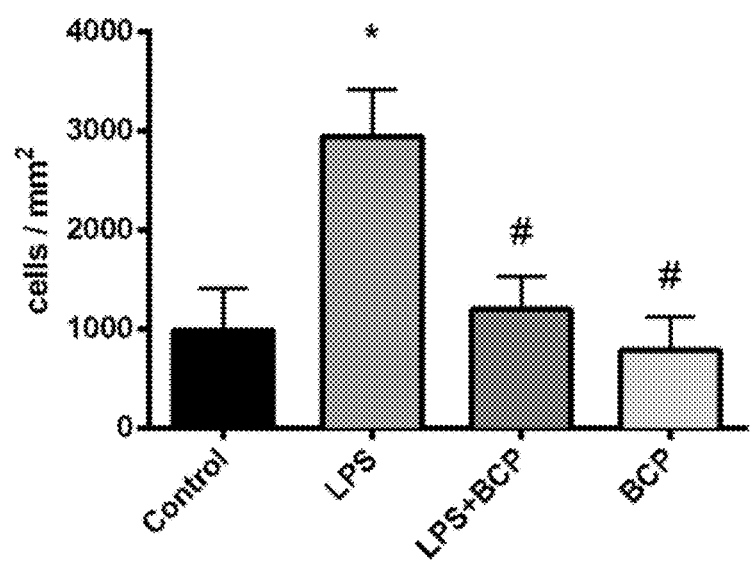
FIG. 14 is a plot showing leukocyte adhesion (cells/mm$^2$) in bladder venules of female BALB/c mice for a lipopolysaccharide (LPS)-induced cystitis model treated with oral beta-caryophyllene (LPS+BCP) in comparison to healthy controls (Control), untreated LPS-induced cystitis (LPS) and healthy controls treated with oral beta-caryophyllene (BCP). Data presented as mean±SD.

FIG. 14 shows the results of leukocyte adhesion in bladder venules of female BALB/c mice for healthy animals (Control, n=5), untreated LPS-induced cystitis (LPS; n=5), LPS-induced cystitis treated with oral Beta-C (100 mg/kg) (LPS+BCP; n=5), and healthy animals administered oral Beta-C (100 mg/kg) (BCP, n=5). Data presented as mean±SD. *$p<0.05$ vs. Control, #$p<0.05$ vs LPS. As shown in FIG. 14, a high level of leukocyte adherence was observed in animals with untreated LPS-induced cystitis. A significant decrease in the number of adherent leukocytes was seen in the group treated with oral BCP. Beta-C in vehicle in healthy animals did not produce any changes in leukocyte adherence.

Oral BCP Administration Increases Functional Capillary Density in Control Animals.

Figure 15:
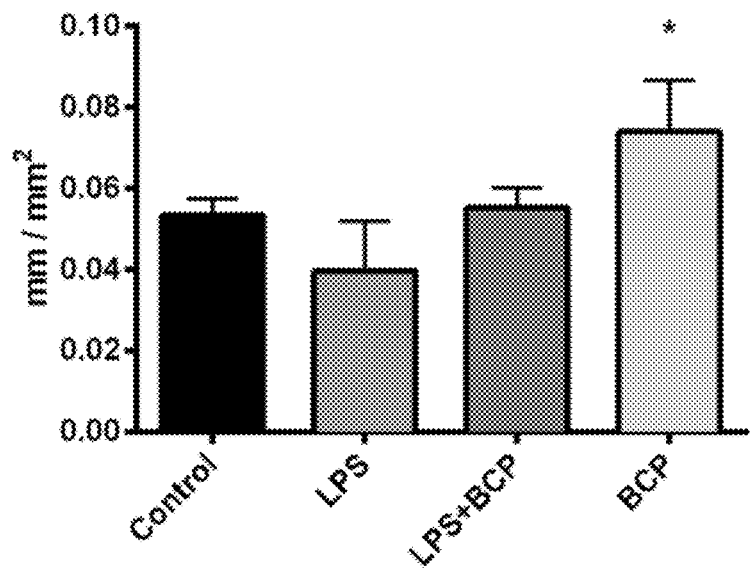
FIG. 15 is a plot showing capillary perfusion (mm/mm$^2$) quantified through functional capillary density (FCD) within the capillaries of female BALB/c mice for a lipopolysaccharide (LPS)-induced cystitis model treated with oral beta-caryophyllene (LPS+BCP) in comparison to healthy controls (Control), untreated LPS-induced cystitis (LPS) and healthy controls treated with oral beta-caryophyllene (BCP). Data presented as mean±SD.

FIG. 15 shows the results of capillary perfusion quantified through functional capillary density (FCD) within the capillaries of female BALB/c mice for healthy animals (Control, n=5), untreated LPS-induced cystitis (LPS; n=5), LPS-induced cystitis treated with oral Beta-C (100 mg/kg) (LPS+BCP; n=5), and healthy animals administered oral Beta-C (100 mg/kg) (BCP, n=5) *$p<0.05$ vs LPS. Data presented as mean±SD. As shown in FIG. 15, no significant differences were observed in the treatment group. There was a significant improvement in FCD in the group treated only with BCP, when compared to endotoxemia group. The results suggest that oral BCP treatment could have the potential to improve FCD, however it was not detectable when compared to the endotoxemia (LPS) group.

Oral BCP and MSM Administration Reduces Leukocyte Adherence in Experimental Cystitis.

Figure 16:
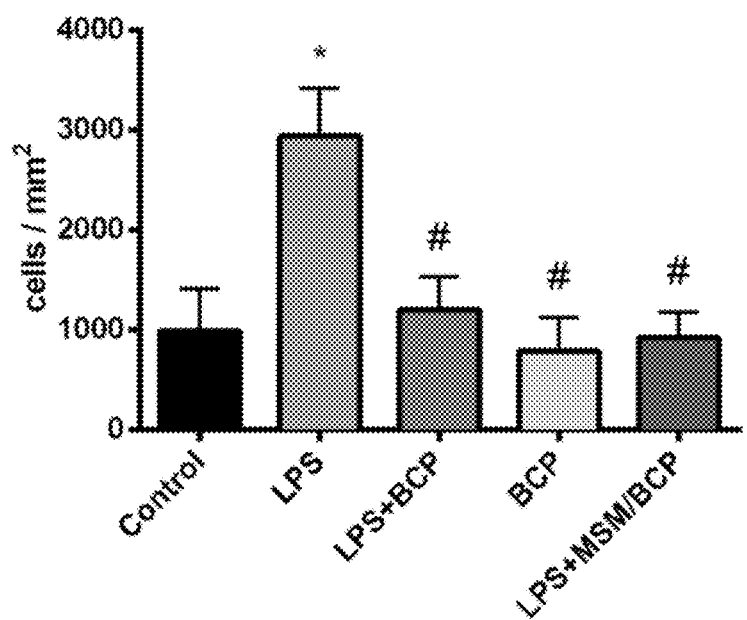
FIG. 16 is a plot showing leukocyte adhesion (cells/mm$^2$) in bladder venules of female BALB/c mice for a lipopolysaccharide (LPS)-induced cystitis model treated with oral beta-caryophyllene (LPS+BCP) or a combination of oral beta-caryophyllene and methylsulfonylmethane (LPS+MSM/BCP) in comparison to healthy controls (Control), untreated LPS-induced cystitis (LPS) and healthy controls treated with oral beta-caryophyllene (BCP). Data presented as mean±SD.

FIG. 16 shows the results of leukocyte adhesion in bladder venules of female BALB/c mice for healthy animals (Control, n=5), untreated LPS-induced cystitis (LPS; n=5), LPS-induced cystitis treated with oral Beta-C (100 mg/kg) (LPS+BCP; n=5), healthy animals administered oral Beta-C (100 mg/kg) (BCP, n=5) and LPS-induced cystitis treated with oral Beta-C (100 mg/kg) and MSM (aqueous solution at 100 mg/kg, prepared the day of the experiment; approximately 0.04 mg/µl in a 20 g animal, ~average weight of an animal used in the study). Data presented as mean±SD. *$p<0.05$ vs. Control, #$p<0.05$ vs LPS. As shown in FIG. 16, a high level of leukocyte adherence was observed in animals with untreated LPS-induced cystitis. A significant decrease in the number of adherent leukocytes was seen in the group treated with oral BCP. Beta-C in vehicle in healthy animals did not produce any significant changes in leukocyte adherence. Animals treated with Beta-C and MSM orally also showed a significant reduction in their level of leukocyte adherence when compared to untreated animals.

Oral BCP and MSM Administration Improves Functional Capillary Density in Experimental Cystitis.

Figure 17:
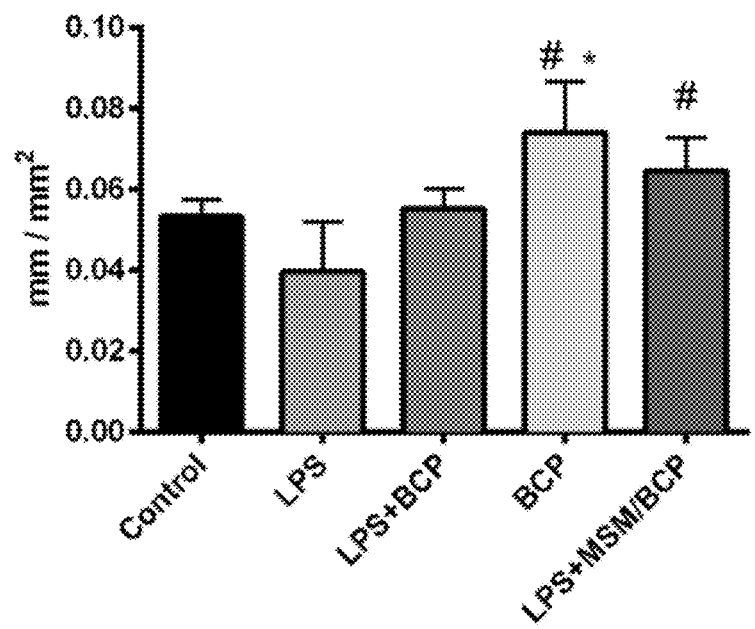
FIG. 17 is a plot showing capillary perfusion (mm/mm$^2$) quantified through functional capillary density (FCD) within the capillaries of female BALB/c mice for a lipopolysaccharide (LPS)-induced cystitis model treated with oral beta-caryophyllene (LPS+BCP) or a combination of oral beta-caryophyllene and methylsulfonylmethane (LPS+MSM/BCP) in comparison to healthy controls (Control), untreated LPS-induced cystitis (LPS) and healthy controls treated with oral beta-caryophyllene (BCP). Data presented as mean±SD.

FIG. 17 shows the results of capillary perfusion quantified through functional capillary density (FCD) within the capillaries of female BALB/c mice for healthy animals (Control, n=5), untreated LPS-induced cystitis (LPS; n=5), LPS-induced cystitis treated with oral Beta-C (100 mg/kg) (LPS+BCP; n=5), healthy animals administered oral Beta-C (100 mg/kg) (BCP, n=5) and LPS-induced cystitis treated with oral Beta-C (100 mg/kg) and MSM (100 mg/kg). Data are presented as mean±SD. As shown in FIG. 17, oral treatment with BCP in MSM restored the functional capillary density back to the levels of control in animals with LPS-induced cystitis. BCP alone did not significantly improve FCD in animals with LPS-induced cystitis. However, a significant improvement in functional capillary density was found in the healthy group treated only with Beta-C, when compared to control group. As mentioned above, these results suggest that oral BCP treatment alone could have the potential to improve FCD, however it was not detectable when compared to the endotoxemia (LPS) group.

BCP and MSM Instillation Reduces Leukocyte Adherence in Experimental Cystitis.

Figure 18:
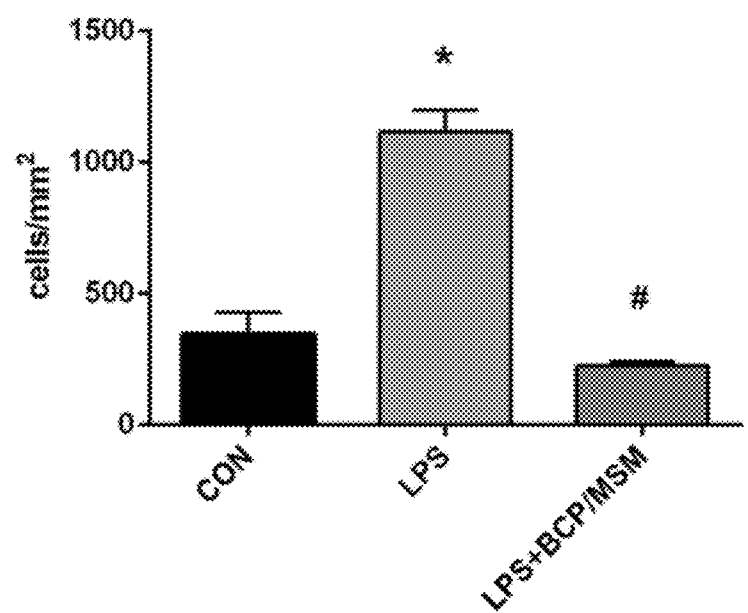
FIG. 18 is a plot showing leukocyte adhesion (cells/mm$^2$) in bladder venules of female BALB/c mice for a lipopolysaccharide (LPS)-induced cystitis model treated with a combination of oral beta-caryophyllene and intravesical 5% methylsulfonylmethane (LPS+MSM/BCP) in comparison to healthy controls (CON) and untreated LPS-induced cystitis (LPS). Data presented as mean±SD.

FIG. 18 shows the results of leukocyte adhesion in bladder venules of female BALB/c mice for healthy animals (CON, n=5), untreated LPS-induced cystitis (LPS; n=5) and LPS-induced cystitis treated with instillation of Beta-C (100 mg/kg) and 5% MSM (LPS+BCP/MSM; n=3). Data presented as mean±SD. *$p<0.05$ vs. Control, #$p<0.05$ vs LPS. As shown in FIG. 18, a high level of leukocyte adherence was observed in animals with untreated LPS-induced cystitis. A significant decrease in the number of adherent leukocytes was seen in the group treated with the combination of oral Beta-C (100 mg/kg) and 5% MSM instillation.

BCP and MSM Instillation Restores Leukocyte Rolling in Experimental Cystitis.

Figure 19:
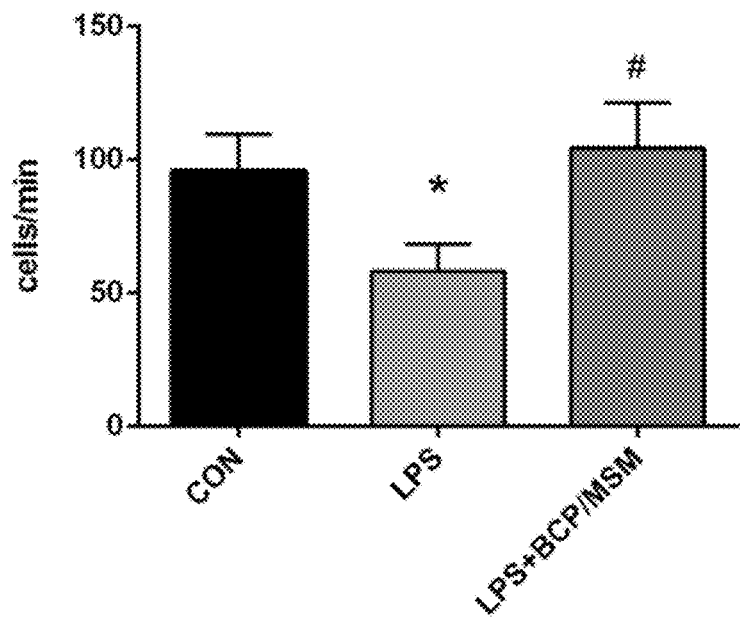
FIG. 19 is a plot showing leukocyte rolling (cells/min) in bladder venules of female BALB/c mice for a lipopolysaccharide (LPS)-induced cystitis model treated with a combination of oral beta-caryophyllene and intravesical 5% methylsulfonylmethane (LPS+MSM/BCP) in comparison to healthy controls (CON) and untreated LPS-induced cystitis (LPS). Data presented as mean±SD.

FIG. 19 shows the results of leukocyte rolling in bladder venules of female BALB/c mice for healthy animals (CON, n=5), untreated LPS-induced cystitis (LPS; n=5) and LPS-induced cystitis treated with instillation of Beta-C (100 mg/kg) and 5% MSM (LPS+BCP/MSM; n=3). Data presented as mean±SD. *$p<0.05$ vs. Control, #$p<0.05$ vs LPS. As shown in FIG. 19, a significant decrease in leukocyte rolling was observed in animals with untreated LPS-induced cystitis. A significant restoration in the number of rolling leukocytes was seen in the group treated with the combination of oral Beta-C (100 mg/kg) and 5% MSM instillation, when compared to the untreated group with LPS-induced cystitis.

BCP and MSM Instillation Restores Functional Capillary Density in Experimental Cystitis.

Figure 20:
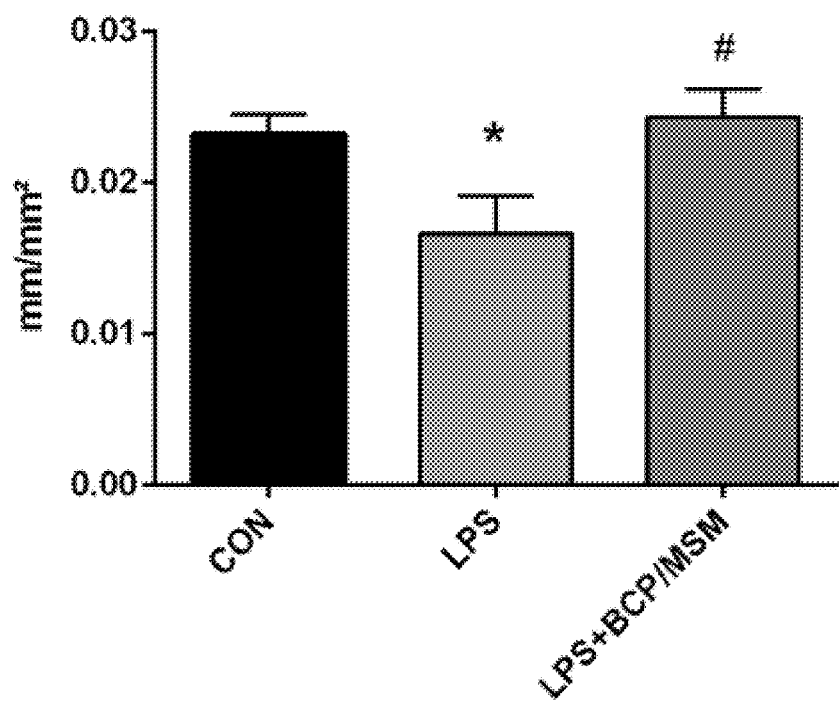
FIG. 20 is a plot showing capillary perfusion (mm/mm$^2$) quantified through functional capillary density (FCD) within the capillaries of female BALB/c mice for a lipopolysaccharide (LPS)-induced cystitis model treated with a combination of oral beta-caryophyllene and intravesical 5% methylsulfonylmethane (LPS+MSM/BCP) in comparison to healthy controls (CON) and untreated LPS-induced cystitis (LPS). Data presented as mean±SD.

FIG. 20 shows the results of capillary perfusion quantified through functional capillary density (FCD) within the capillaries of female BALB/c mice for healthy animals (CON, n=5), untreated LPS-induced cystitis (LPS; n=5) and LPS-induced cystitis treated with instillation of Beta-C (100 mg/kg) and 5% MSM (LPS+BCP/MSM; n=3). Data presented as mean±SD. *p<0.05 vs. Control, #p<0.05 vs LPS. As shown in FIG. 20, a significant decrease in functional perfusion was observed in animals with untreated LPS-induced cystitis. A significant increase in functional perfusion was seen in the group treated with the combination of oral Beta-C (100 mg/kg) and 5% MSM instillation, when compared to the untreated group with LPS-induced cystitis, bringing it back to levels of control animals.

Example 5: Anesthetic Effect of Beta-C

Studies were carried out to investigate the anesthetic effect of oral administration of Beta-C. Animals and local bladder inflammation model were as described hereinabove in Example 2. The groups were as follows:
 1. Healthy Animal Control
 2. LPS (local)
 3. LPS+Beta-C (oral; gavage)
 4. Healthy Animal Control+Beta-C (oral; gavage)

In the oral gavage groups, the mice were treated with 100 mg/kg beta-C by gavage. In the LPS group administered oral beta-C, the administration was 60 minutes prior to LPS exposure. LPS (local) was provided as detailed hereinabove in Example 2.

Pain Assessment Scoring:

Healthy animals were scored behaviourally to set an individual baseline for each specimen. Animals were then anesthetized with isoflurane and given LPS instillation to induce cystitis-like conditions in bladder. After the induction, animals were then woken up and allowed to normally explore/feed themselves in their cage under observation. Changes in behaviour and appearance (i.e. breathing rate, posture, motor activity, eye opening) were then scored again. Each behavioural parameter received a possible maximum score of 10, totaling to a possible maximum of 40. The minimum score possible is a 0, which implies that the parameter is unaffected as a pre-existing condition. Breathing Rate—each decrease in cycle warrants an increase in score. Opening of the eyes—0 complete opening, 5 half opening, 10 fully closed, and 2 and 7 are intermediate positions. Posture—no change is 0, full rounded back OR limp is 10. Intermediate postures gain intermediate scores. Motor activity—activity (exploring, moving, grooming) within 20 seconds. e.g. no movement for 10 seconds (=50%)= 5 points; no movement for 2 seconds (=10%)=1 point. The scoring system is based on that reported by Eschalier et al.[37] but has the additional parameter of motor activity. This was added as something that was significantly noticeable in the study animals with visceral pain.

Electronic Von Frey Aesthesiometry:

This was a quantified pain assessment that measures the amount of force applied in grams, before an animal reacts (e.g. withdraws) to the noxious stimulus. This quantification allows for accurate detection of pain relief effectiveness of a treatment. Healthy animals were scored before any treatments or cystitis induction to set an individual baseline for each specimen. The animals were also scored after the cystitis was induced and the treatment effect could be measured. Each individual animal was compared to itself before the induction, as well as a summarized group comparison was performed.

Statistical Analysis:

Results were analyzed using the software Prism 6 (GraphPad Software, La Jolla, Calif., USA). All data are expressed as means±standard deviation (SD). Following confirmation of normal distribution by Kolmogorov-Smirnov test, groups were tested for significance using one-way analysis of variance (ANOVA) with a Dunnett's post hoc test. Significance was considered at p<0.05.

II. Results and Discussion

Oral BCP Administration Improves Breathing Rate, Eye Opening, Motor Activity and Posture Scores in Experimental Cystitis.

Figure 21:
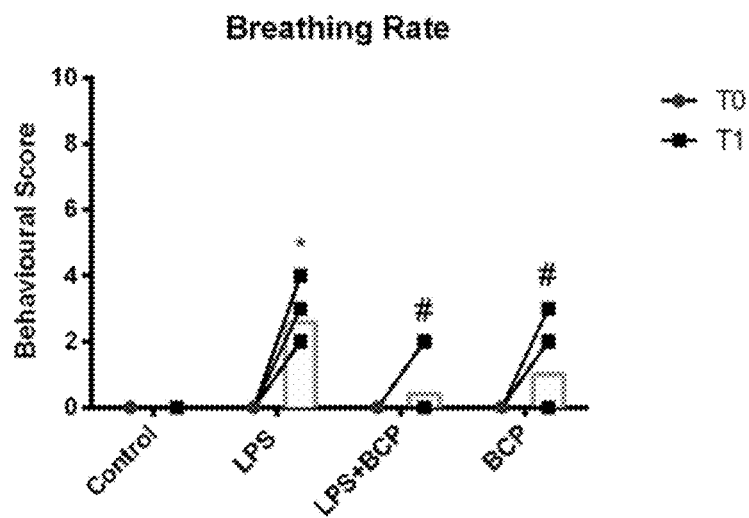
FIG. 21 is a plot showing the behavioural results for breathing rate of female BALB/c mice for a lipopolysaccharide (LPS)-induced cystitis model treated with oral beta-caryophyllene (LPS+BCP) in comparison to healthy controls (Control), untreated LPS-induced cystitis (LPS) and healthy controls treated with oral beta-caryophyllene (BCP). Data presented as individual data points, before cystitis induction (T0) and after (T1), also the mean±SD for each parameter is shown.
Figure 22:
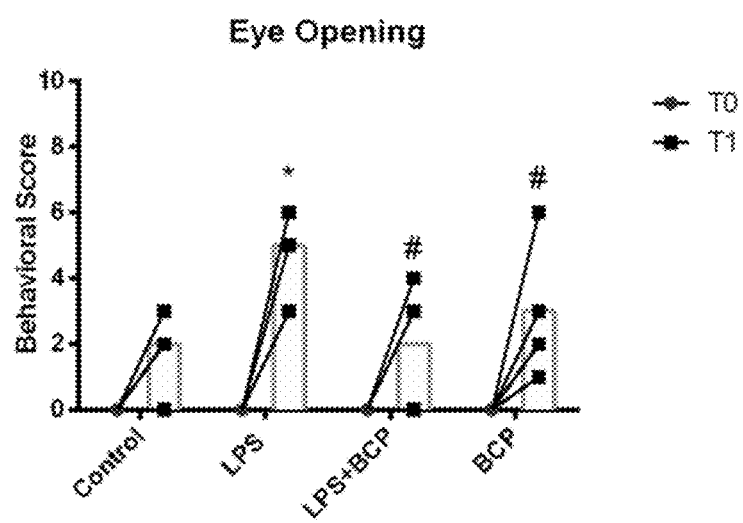
FIG. 22 is a plot showing the behavioural results for eye opening of female BALB/c mice for a lipopolysaccharide (LPS)-induced cystitis model treated with oral beta-caryophyllene (LPS+BCP) in comparison to healthy controls (Control), untreated LPS-induced cystitis (LPS) and healthy controls treated with oral beta-caryophyllene (BCP). Data presented as individual data points, before cystitis induction (T0) and after (T1), also the mean±SD for each parameter is shown.
Figure 23:
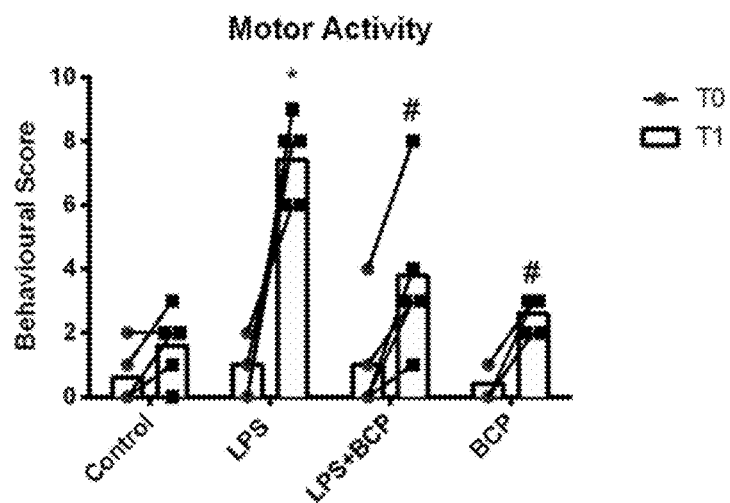
FIG. 23 is a plot showing the behavioural results for motor activity of female BALB/c mice for a lipopolysaccharide (LPS)-induced cystitis model treated with oral beta-caryophyllene (LPS+BCP) in comparison to healthy controls (Control), untreated LPS-induced cystitis (LPS) and healthy controls treated with oral beta-caryophyllene (BCP). Data presented as individual data points, before cystitis induction (T0) and after (T1), also the mean±SD for each parameter is shown.
Figure 24:
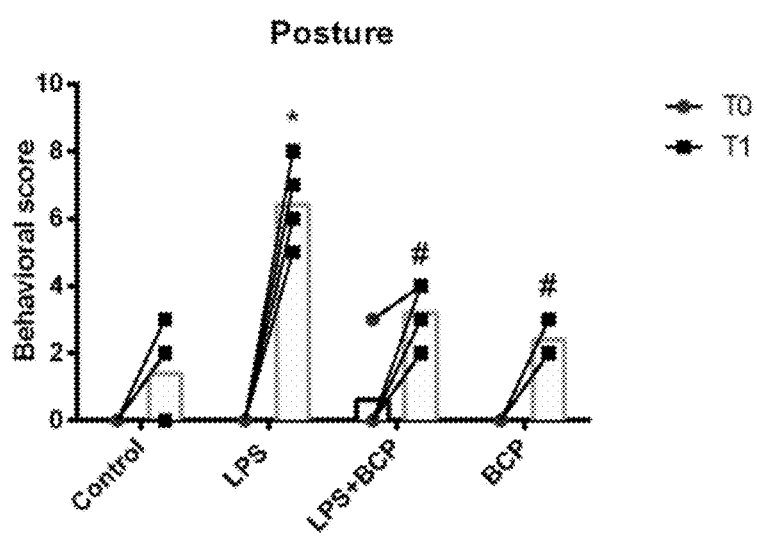
FIG. 24 is a plot showing the behavioural results for posture of female BALB/c mice for a lipopolysaccharide (LPS)-induced cystitis model treated with oral beta-caryophyllene (LPS+BCP) in comparison to healthy controls (Control), untreated LPS-induced cystitis (LPS) and healthy controls treated with oral beta-caryophyllene (BCP). Data presented as individual data points, before cystitis induction (T0) and after (T1), also the mean±SD for each parameter is shown.

FIGS. 21-24 show the individual categories of behavioural results for female BALB/c mice for healthy animals (Control, n=5), untreated LPS-induced cystitis (LPS; n=5), LPS-induced cystitis treated with oral Beta-C (100 mg/kg) (LPS+BCP; n=5) and Beta-C alone, in healthy animals (BCP; n=5). Data presented as individual data points, before cystitis induction (T0) and after (T1), also the mean±SD for each parameter is shown. *p<0.05 vs. Control, #p<0.05 vs LPS. As shown in FIG. 21, a significant increase in breathing rate was observed in animals with untreated LPS-induced cystitis. Treating the animals with Beta-C orally (100 mg/kg) produced a significant reduction in breathing rate. Similarly, the animals with untreated LPS-induced cystitis also showed a poor eye-opening score, with a significant improvement in animals treated with oral BCP (FIG. 22). Significant improvements in motor activity (FIG. 23) and posture (FIG. 24) are also present in animals treated with oral BCP, suggesting an all-around improvement, when compared to untreated animals.

Oral BCP Administration Reduces the Behavioural Pain Score in Experimental Cystitis.

Figure 25:
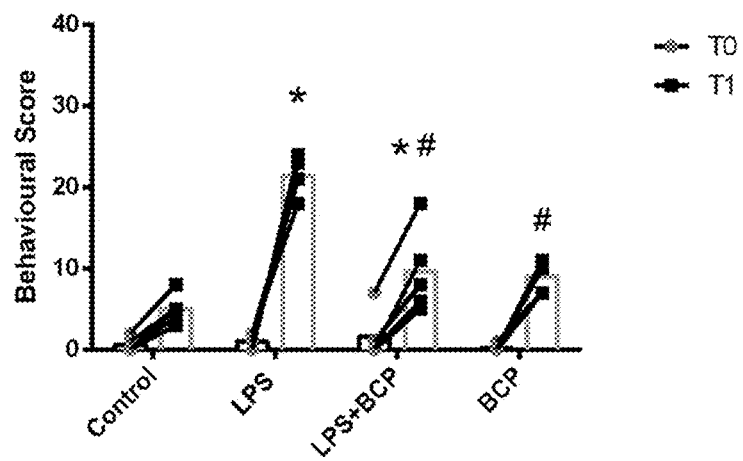
FIG. 25 is a plot showing the total composite score of behavioural results for female BALB/c mice for a lipopolysaccharide (LPS)-induced cystitis model treated with oral beta-caryophyllene (LPS+BCP) in comparison to healthy controls (Control), untreated LPS-induced cystitis (LPS) and healthy controls treated with oral beta-caryophyllene (BCP). Data presented as individual data points with a total score, before cystitis induction (T0) and after the treatment period (T1), also the mean±SD for each group is shown.

FIG. 25 shows the total composite score of behavioural results for female BALB/c mice for healthy animals (Control, n=5), untreated LPS-induced cystitis (LPS; n=5), LPS-induced cystitis treated with oral Beta-C (100 mg/kg) (LPS+BCP; n=5) and BCP alone, in healthy animals (BCP; n=5). Data presented as individual data points with a total score, before cystitis induction (T0) and after the treatment period (T1), also the mean±SD for each group is shown. *p<0.05 vs. Control, #p<0.05 vs LPS. As shown in FIG. 25, a significant increase in behavioural pain score was observed in animals with untreated LPS-induced cystitis. Treating the animals with BCP orally (100 mg/kg) produced a significant reduction in behavioural pain score, suggesting a reduction in levels of discomfort and pain relief.

Oral BCP Administration Increases the Pain Withdrawal Threshold in Experimental Cystitis.

Figure 26:
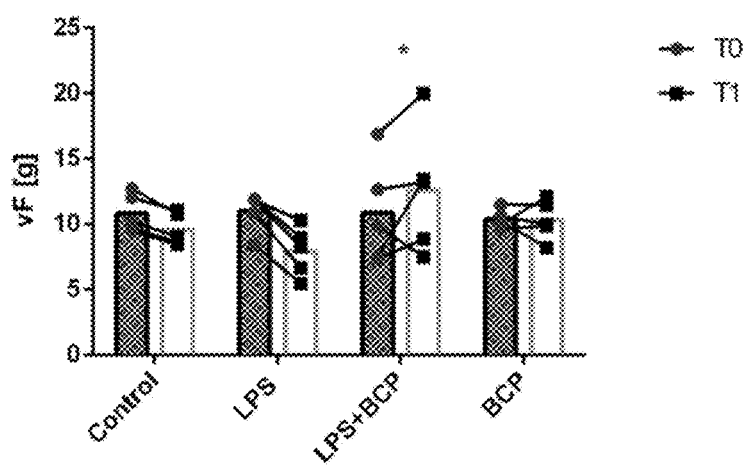
FIG. 26 is a plot showing the amount of force in grams, applied via electronic von Frey aesthesiometer, before a response (e.g. withdrawal) is observed in female BALB/c mice for a lipopolysaccharide (LPS)-induced cystitis model treated with oral beta-caryophyllene (LPS+BCP) in comparison to healthy controls (Control), untreated LPS-induced cystitis (LPS) and healthy controls treated with oral beta-caryophyllene (BCP). Data presented as individual data points with a total force applied, before cystitis induction (T0) and after the treatment period (T1), also the mean±SD for each group is shown.

FIG. 26 shows the amount of force in grams, applied via electronic von Frey aesthesiometer, before a response (e.g. withdrawal) is observed in female BALB/c mice for the following groups: healthy animals (Control, n=5), untreated LPS-induced cystitis (LPS; n=5), LPS-induced cystitis treated with oral BCP (100 mg/kg) (LPS+BCP; n=5) and BCP alone, in healthy animals (BCP; n=5). Data presented as individual data points with a total force applied, before cystitis induction (T0) and after the treatment period (T1), also the mean±SD for each group is shown. *p<0.05 vs. Control. As shown in FIG. 26, a significant increase in applied force was recorded in animals with LPS-induced cystitis, which were treated with oral BCP. Treating the animals with BCP orally (100 mg/kg) produced a significant improvement in withdrawal threshold, suggesting a reduction in levels of discomfort and pain relief.

While the present application has been described with reference to what are presently considered to be the preferred examples, it is to be understood that the application is not limited to the disclosed examples. To the contrary, the present application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

FULL CITATIONS FOR DOCUMENTS REFERRED TO IN THE DESCRIPTION

[1] Clemens, J. Q., Meenan, R. T., Rosetti, M. C. O. K., Gao, S. Y., & Calhoun, E. A. (2005). Prevalence and incidence of interstitial cystitis in a managed care population, 173 (January), 98-102.

[2] Grover, S., Srivastava, A., Lee, R., Tewari, A. K., & Te, A. E. (2011). Role of inflammation in bladder function and interstitial cystitis, 19-33.

[3] Parsons, C., Benson, G., Childs, S., Hanno, P., Sant, G., & Webster, G. (1993). A quantitatively controlled method to study prospectively interstitial cystitis and demonstrate the efficacy of pentosanpolysulfate. *Journal of Urology,* 150(3), 845-848.

[4] Lee, C.-L., & Kuo, H.-C. (2015). Long-Term Efficacy and Safety of Repeated Intravescial OnabotulinumtoxinA Injections Plus Hydrodistention in the Treatment of Interstitial Cystitis/Bladder Pain Syndrome. *Toxins,* 7, 4283-4293.

[5] (a) Shirley, S. W., Stewart, B. H., & Mirelman, S. (1978) Dimethyl sulfoxide in treatment of inflammatory genitourinary disorders. *Urology,* 11(3): 215-220; (b) Rössberger, J., Fall, M., & Peeker, R. (2005) Critical appraisal of dimethyl sulfoxide treatment for interstitial cystitis discomfort, side-effects and treatment outcome. *Scandinavian journal of urology and nephrology,* 39(1): 73-77.

[6] (a) Hung, M., Chen, Y., & Shen, P. (2012). Risk factors that affect the treatment of interstitial cystitis using intravesical therapy with a dimethyl sulfoxide cocktail, 1533-1539; (b) Lim, Y. N., Dwyer, P., Murray, C., Karmakar, D., Rosamilia, A., & Thomas, E. (2016). Long-term outcomes of intravesical dimethyl sulfoxide/heparin/hydrocortisone therapy for interstitial cystitis/bladder pain syndrome. *International Urogynecology Journal*; (c) Rawls, W. F., Cox, L., & Rovner, E. S. (2017). Dimethyl sulfoxide (DMSO) as intravesical therapy for interstitial cystitis/bladder pain syndrome: A review, (September 2016), 1-8.

[7] (a) Butawan, M., Benjamin, R. L. & Bloomer, R. J. Methylsulfonylmethane: Applications and safety of a novel dietary supplement *Nutrients* 2017, 9, 290; doi: 10.3390/nu9030290. (b) Childs, S. J. Dimethyl sulfone ($DMSO_2$) in the treatment of interstitial cystitis. *Urol. Clin. N. Am.* 1994, 21, 85-88.

[8] (a) De Petrocellis, L., & Di Marzo, V. (2009). An introduction to the endocannabinoid system: from the early to the latest concepts. *Best Practice & Research Clinical Endocrinology & Metabolism,* 23, 1-15; (b) Pandey, R., Mousawy, K., Nagarkatti, M., & Nagarkatti, P. (2009). Endocannabinoids and immune regulation. *Pharmacol Res,* 60(2), 85-92.

[9] Pertwee, R. G., & Ross, R. A. (2002). Cannabinoid receptors and their ligands. *Prostaglandins Leukot Essent Fatty Acids,* 66(2-3), 101-121.

[10] (a) Hayn, M. H., Ballesteros, I., de Miguel, F., Coyle, C. H., Tyagi, S., Yoshimura, N., Chancellor, M. B., & Tyagi, P. (2008). Functional and Immunohistochemical Characterization of CB1 and CB2 Receptors in Rat Bladder. *Urology,* 72(5), 1174-1178; (b) Klein, T. W. (2005). Cannabinoid-based drugs as anti-inflammatory therapeutics. *Nature Reviews Immunology,* 5(5), 400-411.

[11] Pertwee, R. G. (2006). The pharmacology of cannabinoid receptors and their ligands: an overview. *International Journal of Obesity,* 30, S13-S18.

[12] Munro, S., Thomas, K., & Abu-Shaar, M. (1993). Molecular Characterization of a peripheral receptor for cannabinoids. *Nature,* 365.

[13] (a) Zajicek, J., Sanders, H. P., Vickery, J., Ingram, W. M., Reilly, S. M., Nunn, A. J., Teare, L. J., Fox, P. J., & Thompson, A. J. (2005). Cannabinoids in multiple sclerosis (CAMS) study: safety and efficacy data for 12 months follow up. *J Neurol Neurosurg Psychiatry,* 1664-1669; (b) Zajicek, J., Fox, P., Sanders, H., Wright, D., Vickery, J., Nunn, A., & Thompson, A. (2003). Cannabinoids for treatment of spasticity and other symptoms related to multiple sclerosis (CAMS study): multicentre randomised placebo-controlled trial. *Lancet,* 362, 1517-1526.

[14] (a) Gratzke, C., Streng, T., Park, A., Christ, G., Stief, C. G., Hedlund, P., & Andersson, K. (2009). Distribution and Function of Cannabinoid Receptors 1 and 2 in the Rat, Monkey and Human Bladder. *JURO,* 181(4), 1939-1948; (b) Hayn, M. H., Ballesteros, I., Miguel, F. De, Coyle, C. H., Tyagi, S., Yoshimura, N., Chancellor, M. B., & Tyagi, P. (2008). Functional and Immunohistochemical Characterization of CB1 and CB2 Receptors in Rat Bladder. *JURO,* 3-7.

[15] Wang, Z., Wang, P., & Bjorling, D. E. (2013). Activation of cannabinoid receptor 2 inhibits experimental cystitis. *American Journal of Physiology. Regulatory, Integrative and Comparative Physiology,* 304, 846-853.

[16] Farquhar-Smith, W. P., Jaggar, S. I., & Rice, A. S. C. (2002). Attenuation of nerve growth factor-induced visceral hyperalgesia via cannabinoid CB1 and CB2-like receptors. *Pain,* 97(1-2), 11-21.

[17] Jaggar, S. I., Hasnie, F. S., Sellaturay, S., & Rice, A. S. C. (1998). The anti-hyperalgesic actions of the cannabinoid anandamide and the putative CB2 receptor agonist palmitoylethanolamide in visceral and somatic inflammatory pain. *Pain,* 76(1-2), 189-199.

[18] Tambaro, S., Antonietta, M., Mastinu, A., & Lazzari, P. (2014). Evaluation of selective cannabinoid CB 1 and CB 2 receptor agonists in a mouse model of lipopolysaccharide-induced interstitial cystitis. *European Journal of Pharmacology,* 729, 67-74.

[19] (a) Merriam, F., Wang, Z., Guerios, S., & Bjorling, D. (2015). Cannabinoid receptor 2 is increased in acutely and chronically inflamed bladder of rats. *Neuroscience Letters,* 445(1), 130-134; (b) Wang, Z., Wang, P., & Bjorling, D. E. (2013). Activation of cannabinoid receptor 2 inhibits experimental cystitis. *American Journal of Physiology. Regulatory, Integrative and Comparative Physiology,* 304, 846-853; (c) Wang, Z., Wang, P., & Bjorling, D. E. (2014). Treatment with a Cannabinoid Receptor 2 Agonist Decreases Severity of Established Cystitis. *Journal of Urology*, 191(4), 1153-1158.

[20] (a) Klauke, A.-L., Racz, I., Pradier, B., Markert, A., Zimmer, A. M., Gertsch, J., & Zimmer, A. (2014). The cannabinoid CB2 receptor-selective phytocannabinoid beta-caryophyllene exerts analgesic effects in mouse models of inflammatory and neuropathic pain. *European Neuropsychopharmacology*, 24(4), 608-620; (b) Gertsch, J., Leonti, M., Raduner, S., Racz, I., Chen, J.-Z., Xie, X.-Q., Altmann, K.-H., Karsak, M., & Zimmer, A. (2008). Beta-caryophyllene is a dietary cannabinoid. *Proceedings of the National Academy of Sciences of the United States of America*, 105(26), 9099-104.

[21] Ghelardini, C., Galeotti, N., Di Cesare Mannelli, L., Mazzanti, G., & Bartolini, A. (2001). Local anaesthetic activity of β-caryophyllene. *Il Farmaco*, 56(5), 387-389.

[22] See, for example: Graham, E., & Chai, T. C. (2006) Dysfunction of bladder urothelium and bladder urothelial cells in interstitial cystitis. *Current urology reports*, 7(6), 440-446.

[23] See, for example: Chiu, I. M., Von Hehn, C. A., & Woolf, C. J. (2012) Neurogenic inflammation and the peripheral nervous system in host defense and immunopathology. *Nature neuroscience*, 15(8), 1063-1067.

[24] See, for example: Costigan, M., Scholz, J. & and Woolf, C. J. (2009) Neuropathic pain: a maladaptive response of the nervous system to damage. *Annual review of neuroscience*, 32: 1-32.

[25] Jerde, T. J., Bjorling, D. E., Steinberg, H., Warner, T., & Saban, R. (2000). Determination of mouse bladder inflammatory response to E. coli lipopolysaccharide. *Urological research*, 28(4), 269-73.

[26] (a) Sant, G. R., Kempuraj, D., Marchand, J. E., & Theoharides, C. (2007). The Mast Cell in Interstitial Cystitis: Role in Pathophysiology and Pathogenesis; (b) Theoharides, C., Kempuraj, D., & Sant, G. R. (2001). Mast cell involvement in interstitial cystitis: a review of human and experimental evidence. *Urology*, 57(6), 47-55; (c) Wang, X., Liu, W., Donnell, M. O., Lutgendorf, S., Bradley, C., Schrepf, A., Liu, L., Kreder, K., & Luo, Y. (2016). Evidence for the Role of Mast Cells in Cystitis-Associated Lower Urinary Tract Dysfunction: A Multidisciplinary Approach to the Study of Chronic Pelvic Pain Research Network Animal Model Study, 1-12.

[27] Marone, G., Galli, S. J., & Kitamura, Y. (2002). Probing the roles of mast cells and basophils in natural and acquired immunity, physiology and disease. *Trend in Immunology*, 23(9), 425-427.

[28] (a) Horny, H., Menke, D., & Kaiserling, E. (1996). Neoplastic human tissue mast cells express the adhesion molecule CD44/HCAM. *Virchows Archiv: an international journal of pathology*, 429(2-3), 91-94; (b) Suzuki, H., Miura, S., Liu, Y., Tsuchiya, M., & Ishii, H. (1995). Substance P induces degranulation of mast cells and leukocyte adhesion to venular endothelium. *Peptides*, 16(8), 1447-1452; (c) Yasuda, M., Hasunuma, Y., Adachi, H., Sekine, C., Sakanishi, T., Hashimoto, H., Ra, C., Yagita, H., & Okumura, K. (1995). Expression and function of fibronectin binding integrins on rat mast cells. *International Immunology*, 7(2), 251-258.

[29] Green, M., Fillippou, A., Sant, G., & Theoharides, C. (2004). Expression of Intracellular Adhesion Molecules in The Bladder of Patients with Interstitial Cystitis. *Urology*, 63, 688-693.

[30] McCurdy, J., Lin, T., & Marshall, J. (2001). Toll-like receptor 4-mediated activation of murine mast cells. *Journal of Leukocyte Biology*, 70(6), 977-984.

[31] Spronk, P. E., Zandstra, D. F., & Ince, C. (2004). Bench-to-bedside review: sepsis is a disease of the microcirculation. *Critical care (London, England)*, 8(6), 462-468.

[32] (a) Astiz, M., DeGent, G., Lin, R., & Rackow, E. (1995). Microvascular function and rheologic changes in hyperdynamic sepsis. *Critical care medicine*, 23(2), 265-271; (b) Spronk, P. E., Zandstra, D. F., & Ince, C. (2004). Bench-to-bedside review: sepsis is a disease of the microcirculation. *Critical care (London, England)*, 8(6), 462-468.

[33] Yeh, Y., Ko, W., Chan, K., Fan, S., Tsai, J., Cheng, Y., & Sun, W. (2012). Effects of eritoran tetrasodium, a toll-like receptor 4 antagonist, on intestinal microcirculation in endotoxemic rats. *Shock*, 37(5), 556-561.

[34] (a) Akira, S., & Takeda, K. (2004). Toll-Like Receptor Signalling. *Nature reviews. Immunology*, 4 (July); (b) Cho, J., & Kim, S. (2009). A Novel Mitogen-Activated Protein Kinase Mechanism of Gene Transrepression by GR. *Molecular Endocrinology*, 23 (January), 86-99; (c) Johnson, G. L., & Lapadat, R. (2002). Mitogen-Activated Protein Kinase Pathways Mediated by ERK, JNK, and p38 Protein Kinases The Protein Kinase Complement of the Human Genome. *Science*, 298 (December).

[35] Liu, H., & Kuo, H. (2016). Urological Science Biomarkers for patients with interstitial cystitis/bladder. *Urological Science*, 26(4), 225-229.

[36] (a) Facchinetti, F., Giudice, E. D. E. L., & Furegato, S. (2003). Cannabinoids Ablate Release of TNF-α in Rat Microglial Cells Stimulated. *Glia*, 168 (March 2002), 161-168; (b) Lehmann, C., Kianian, M., Zhou, J., Küster, I., Kuschnereit, R., Whynot, S., Hung, O., Shukla, R., Johnston, B., Cerny, V., Pavlovic, D., Spassov, A., & Kelly, M. E. (2012). Cannabinoid receptor 2 activation reduces intestinal leukocyte recruitment and systemic inflammatory mediator release in acute experimental sepsis. *Critical care (London, England)*, 16(2), R47; (c) Molina-holgado, F., Molina-holgado, E., Guaza, C., & Rothwell, N. J. (2002). Role of CB 1 and CB 2 Receptors in the Inhibitory Effects of Cannabinoids on Lipopolysaccharide-Induced Nitric Oxide Release in Astrocyte Cultures, 836, 829-836.

[37] Boucher, M., Meen, M., Codron, J. P., Coudore, F, Kemeny, J. L., & Eschalier A., "Cyclophosphamide-induced cystitis in freely-moving conscious rats: behavioral approach to a new model of visceral pain" 2000 *J Urol*. July; 164(1):203-8.

The invention claimed is:

1. A method of treating interstitial cystitis in a subject, the method comprising administering a CB2 target agent local anaesthetic and an additional agent to the subject,
    wherein the CB2 target agent local anaesthetic is a CB2 orthosteric agonist agent local anaesthetic agent that is beta-caryophyllene, and
    wherein the additional agent is dimethyl sulfoxide (DMSO) or methylsulfonylmethane (MSM) administered as an aqueous solution comprising about 5% to about 40% of DMSO or about 5% to about 40% of MSM.

2. The method of claim 1, wherein the additional agent is dimethyl sulfoxide.

3. The method of claim 2, wherein the dimethyl sulfoxide is administered intravesically.

4. The method of claim 3, wherein the aqueous solution comprises about 5% dimethyl sulfoxide.

5. The method of claim 1, wherein the additional agent is methylsulfonylmethane.

6. The method of claim 5, wherein the methylsulfonylmethane is administered intravesically as an aqueous solution comprising about 5% methylsulfonylmethane.

7. The method of claim 5, wherein the methylsulfonylmethane is administered orally.

8. The method of claim 1, wherein the CB2 target agent local anaesthetic is administered orally.

9. The method of claim 8, wherein the oral administration is in the form of a capsule comprising the CB2 target agent local anaesthetic.

10. The method of claim 9, wherein the CB2 target agent local anaesthetic is administered in combination with methylsulfonylmethane and the capsule further comprises the methylsulfonylmethane.

11. The method of claim 1, wherein the CB2 target agent local anaesthetic is administered topically.

12. The method of claim 11, wherein the topical administration is in the form of a topical cream comprising the CB2 target agent local anaesthetic.

13. The method of claim 1, wherein the CB2 target agent local anaesthetic is administered intravesically.

14. The method of claim 13, wherein the CB2 target agent local anaesthetic is administered in combination with dimethyl sulfoxide and the intravesical administration is in the form of an aqueous solution comprising the CB2 target agent local anaesthetic and the dimethyl sulfoxide.

15. The method of claim 13, wherein the CB2 target agent local anaesthetic is administered in combination with methylsulfonylmethane and the intravesical administration is in the form of an aqueous solution comprising the CB2 target agent local anaesthetic and the methylsulfonylmethane.

16. The method of claim 1, wherein the subject is human.

17. The method of claim 16, wherein the subject is female.

* * * * *